US010792153B2

(12) United States Patent
Solem et al.

(10) Patent No.: US 10,792,153 B2
(45) Date of Patent: Oct. 6, 2020

(54) IMPLANTABLE CARDIAC VALVE IMPROVEMENT DEVICE, SYSTEM AND PROCEDURE

(71) Applicant: Syntach AG, Schaffhausen (CH)

(72) Inventors: Kristian Solem, Trelleborg (SE); Jan Otto Solem, Bjärred (SE); Daniel Engvall, Halmstad (SE); Victoria Krüger, Oxie (SE); Martin Wolff, Lund (SE); Jonathan Berg, Furulund (SE); André Spånberg, Lund (SE)

(73) Assignee: Syntach AG (CH)

( * ) Notice: Subject to any disclaimer, the term of this patent is extended or adjusted under 35 U.S.C. 154(b) by 178 days.

(21) Appl. No.: 16/031,732

(22) Filed: Jul. 10, 2018

(65) Prior Publication Data

US 2020/0015969 A1   Jan. 16, 2020

(51) Int. Cl.
*A61F 2/24* (2006.01)
*A61B 17/04* (2006.01)

(52) U.S. Cl.
CPC .......... *A61F 2/2445* (2013.01); *A61F 2/2451* (2013.01); *A61F 2/2463* (2013.01); *A61B 2017/0464* (2013.01); *A61F 2/246* (2013.01); *A61F 2/2454* (2013.01); *A61F 2210/0014* (2013.01); *A61F 2250/006* (2013.01)

(58) Field of Classification Search
CPC ..... A61F 2/2442; A61F 2/2445; A61F 2/2448
See application file for complete search history.

(56) References Cited

U.S. PATENT DOCUMENTS

| 2005/0004668 | A1* | 1/2005 | Aklog ................ A61F 2/2448 623/2.36 |
| 2005/0070999 | A1 | 3/2005 | Spence |
| 2007/0067029 | A1* | 3/2007 | Gabbay ............... A61F 2/2409 623/2.13 |
| 2013/0006352 | A1 | 1/2013 | Yaron |
| 2013/0282110 | A1 | 10/2013 | Schweich, Jr. et al. |
| 2016/0151552 | A1 | 6/2016 | Solem |
| 2017/0128203 | A1 | 5/2017 | Zhang et al. |
| 2017/0245993 | A1 | 8/2017 | Gross et al. |

FOREIGN PATENT DOCUMENTS

| EP | 3017792 A1 | 5/2016 |
| EP | 3017792 A1 | 11/2016 |

OTHER PUBLICATIONS

International Search Report and Written Opinion as issued in connection with International Patent Application No. PCT/EP2019/068595, dated Nov. 10, 2019, 15 pages.

* cited by examiner

*Primary Examiner* — Jason-Dennis N Stewart

(57) ABSTRACT

An implantable medical device is disclosed including an anchor unit configured to be permanently anchored at a cardiac valve of a patient, at least one locking unit, such as for fixation of tissue of the cardiac valve and/or fixation of at least a part of a shape of the anchor unit, and at least one coupling unit for connecting the anchor unit to at least one of the locking unit. The coupling unit has a first end portion and a second end portion, wherein the first end portion is connectable to the anchor unit, and the second end portion includes the locking unit.

20 Claims, 11 Drawing Sheets

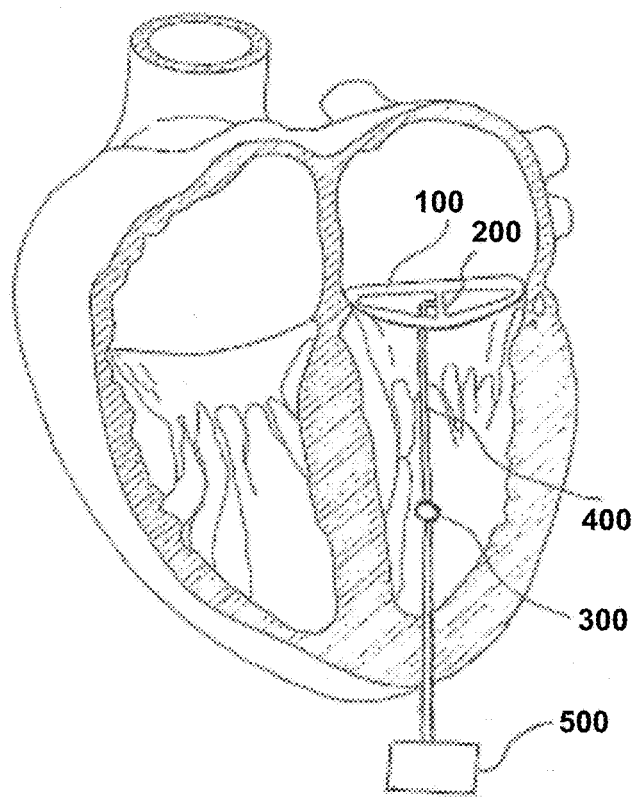
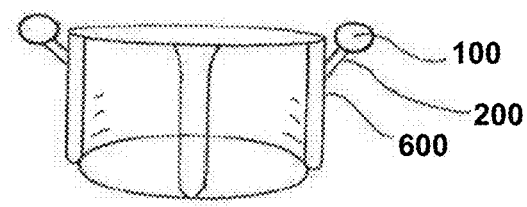
Fig. 7a
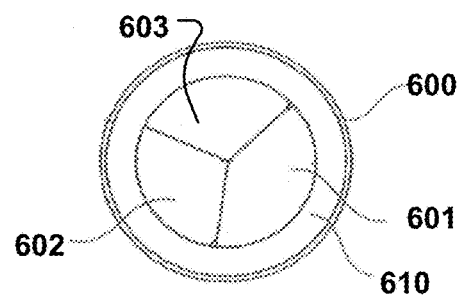
Fig. 7b
Fig. 6
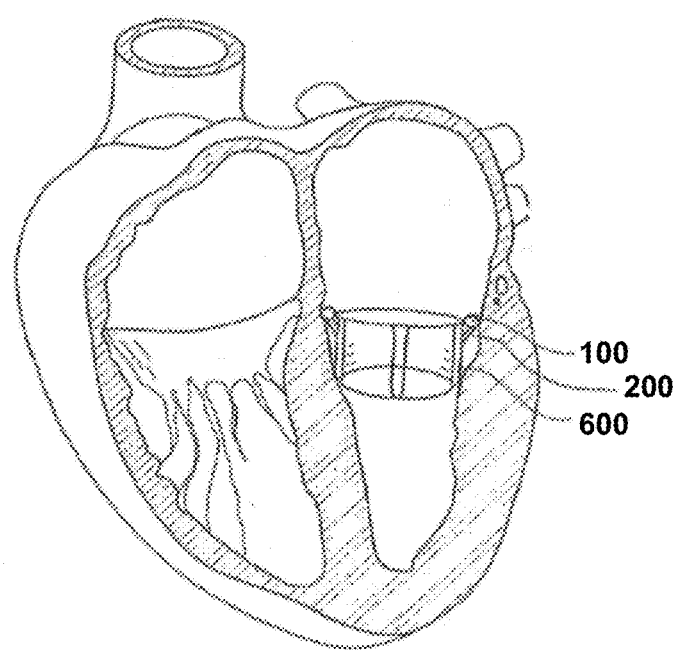
Fig. 7c

IMPLANTABLE CARDIAC VALVE IMPROVEMENT DEVICE, SYSTEM AND PROCEDURE

BACKGROUND OF THE INVENTION

Field of the Invention

This invention pertains in general to the field of medical implantable devices for improving function of a cardiac valve.

Description of Prior Art

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

The combination of severe mitral valve regurgitation in combination with chronic heart failure is frequent and causes high mortality among elderly patients. Typically, annuloplasty rings have been implanted during open heart surgery, so the annuloplasty ring can be sewn into the valve annulus. Most commonly, a reshaping of the annulus is performed, e.g. by introducing a reshaping device in the coronary sinus surrounding the mitral valve annulus. The shape is then fixated by an annuloplasty ring being affixed to the annulus tissue. Several concepts are pursued, but all suffer from drawbacks.

For instance, some implanted annular repair rings, and in particular U-shaped or open repair rings, have a tendency to widen over time, and allow recurrent valve regurgitation to occur.

In addition to that, many leaking valves are in such a bad shape that the leakage cannot be fixed with a repair ring alone. Many repaired valves have for instance, despite performed annuloplasty, insufficient coaptation of valve leaflets when they close. Conventional devices are stand-alone rings that are not protected against widening and with no possibility to attach leaflets against restrainment or prolapse. There is a need to provide a medical device which advantageously solves the issue with insufficient coaptation of valve leaflets upon performed annuloplasty.

Other devices are clips alone, e.g. a MitraClip that attaches anterior and posterior mitral valve leaflets to each other to treat mitral valve regurgitation, and septal, anterior and posterior tricuspidalis leaflets to treat tricuspidalis insufficiency, most commonly for patients who should not have open-heart surgery. These devices could be improved further, e.g. by providing a long term stable reshaping of a leaflet annulus. Thus, there is a need for a new device that allows a synergistic combination of annuloplasty by means of a secure ring that does not widen, a secure attachment between valve leaflets in order to get a good coaptation, and at the same time allow a cardiac assist device to attach to a heart valve plane.

Assist devices that attach to and support atrio-ventricular plane movement are under development. They allow a totally implantation under the skin and charging transcutaneously. A secure and efficient valve plane movement would be advantageous.

Hence, an improved device, system, or medical procedure for secure valve repair or replacement would be advantageous, in particular allowing for increased flexibility, cost-effectiveness, better survival for cases with advanced chronic heart failure, in particular in connection with mitral insufficiency. Also, an improved system for allowing secure valve repair and advantageous cardiac assist, i.e. mechanical circulatory support would be advantageous.

Some examples disclosed herein provide a medical device which advantageously solves the issue with insufficient coaptation of valve leaflets upon performed annuloplasty. Such means include means described in the here presented medical device, such as a locking unit as a mean attached in order to fixate tissue, especially valve leaflet tissue.

Some examples of medical devices disclosed herein have the ability to both stabilizing a repair ring against widening and at the same time attach leaflets to each other in order to secure a good coaptation of valve leaflets. Some examples of medical devices disclosed herein provide for improved secure valve repair and secure connection to a cardiac assist, i.e. mechanical circulatory support, device.

SUMMARY OF THE INVENTION

Accordingly, embodiments of the present invention preferably seek to mitigate, alleviate or eliminate one or more deficiencies, disadvantages or issues in the art, such as the above-identified, singly or in any combination by providing a devices, systems, and methods according to the appended independent patent claims. Further embodiments of the invention are defined in the dependent claims, wherein features for the second and subsequent aspects of the invention are as for the first aspect mutatis mutandis. The disclosure may include further inventions not presently claimed.

In an aspect of the disclosure, an implantable medical device is provided, which includes at least one anchor unit that is permanently anchored at a cardiac valve of a patient, when implanted. The device further includes at least one locking unit. The locking unit is preferably providing fixation of tissue of the cardiac valve. Alternatively, or in addition, the locking unit is providing fixation of at least a part of a shape of the anchor unit. The device further includes at least one coupling unit for connecting the anchor unit to at least one locking unit. The coupling unit has a first end portion and a second end portion, wherein the first end portion is connectable to the anchor unit, and when implanted connected thereto. The second end portion includes in some embodiments the locking unit.

In an aspect of the disclosure, an implantable medical device is provided that includes a flexible anchor unit including an annuloplasty implant. The annuloplasty implant is, when implanted, permanently anchored at an annulus of a cardiac valve of a patient. The medical device further includes at least one locking unit and at least one coupling unit for connecting the anchor unit to the at least one locking unit. The coupling unit preferably includes at least one lockable arm, and has a first end portion and a second end portion. The first end portion is connectable to the anchor unit, and when implanted connected thereto. The second end portion includes the locking unit. In this manner, such at least a part of a shape of the anchor unit is fixed when the anchor unit, coupling unit and locking unit are connected for stabilizing the anchor unit at the annulus.

In an aspect of the disclosure, an implantable medical device is provided that includes an anchor unit permanently anchored at a cardiac valve of a patient, when implanted. The device further includes at least one locking unit for fixation of tissue of the cardiac valve, and at least one coupling unit for connecting the anchor unit to at least one locking unit. The coupling unit has a first end portion. The coupling unit is, when implanted, connected at the first end portion to the anchor unit and connected remote of the first end portion to the tissue of the cardiac valve by the locking unit.

In an aspect of the disclosure, a system is provided. The system includes an implantable medical device including an anchor unit to be permanently anchored at a cardiac valve of a patient, at least one locking unit, and at least one coupling unit for connecting the anchor unit to at least one locking unit. The coupling unit is preferably at least one arm and has a first end portion and a second end portion. The first end portion is connectable to the anchor unit, and the second end portion includes the locking unit. The system further includes a driving unit, for example a driving unit of a cardiac assist device, which is releasably or permanently connected to the at least one coupling unit, at the second end portion by the locking unit.

In an aspect of the disclosure, a system is provided. The system includes an implantable medical device including an anchor unit configured to be permanently anchored at a cardiac valve of a patient. The system includes at least one locking unit. The system includes at least one coupling unit for connecting the anchor unit to at least one locking unit. The coupling unit is preferably at least one arm. The coupling unit has a first end portion and a second end portion, wherein the first end portion is connectable to the anchor unit. The second end portion preferably includes the locking unit. The system further includes a further unit, such as a cardiac valve replacement or repair unit. The anchor unit is connected to the further unit, such as a cardiac valve replacement or repair unit, preferably being connected to each other via said at least one coupling unit.

In an aspect of the disclosure, a delivery system is provided. The delivery system includes a delivery catheter that has loaded in one of its interior lumen at least one coupling unit for insertion into heart cavities such as a left or right atrium of a heart. The coupling unit is either attached to an anchor unit also loaded inside the delivery catheter or can be attached to a previously implanted anchor unit. The delivery system may also include a locking unit and/or an extension unit for delivery to the heart.

In an aspect of the disclosure, a medical procedure of implanting a medical device described herein is disclosed. The procedure includes providing a delivery system as described herein, navigating with a delivery catheter of the delivery system to a delivery site adjacent to a cardiac valve of a patient. An anchor unit and/or at least one coupling means at said delivery site, securing said coupling unit by an attachment unit to said anchor unit, advancing a locking unit through said delivery catheter to said coupling unit, and fixating said coupling unit securely by said locking unit.

In an aspect of the disclosure, a method of improving function of a cardiac valve is provided. The method includes one or more of a) stabilizing a flexible annuloplasty implant (see e.g. FIGS. 4a), b), c), and d));
b) fixation of cardiac tissue to an annuloplasty implant (see e.g. FIGS. 5a) and b));
c) providing cardiac assist by connecting a cardiac assist device to an annuloplasty implant, (see e.g. FIG. 6); and/or
d) connecting the anchor unit to a cardiac valve replacement or repair unit (see e.g. FIG. 7a), b), and c), FIG. 8a), b), c), d), e), f), and g)).

BRIEF DESCRIPTION OF THE DRAWINGS

FIG. 6 is a cross section view of a heart illustrating a coupling unit that includes an extension unit as well as a cardiac assist device.

FIG. 7a-b are schematic illustrations of an artificial heart valve in a cage replacing the native heart valve when integrated in examples of an anchored system.

FIG. 7c is a schematic illustration of an artificial heart valve when implanted and coupled to an anchor unit.

DESCRIPTION OF THE PREFERRED EMBODIMENTS

Figure 1:
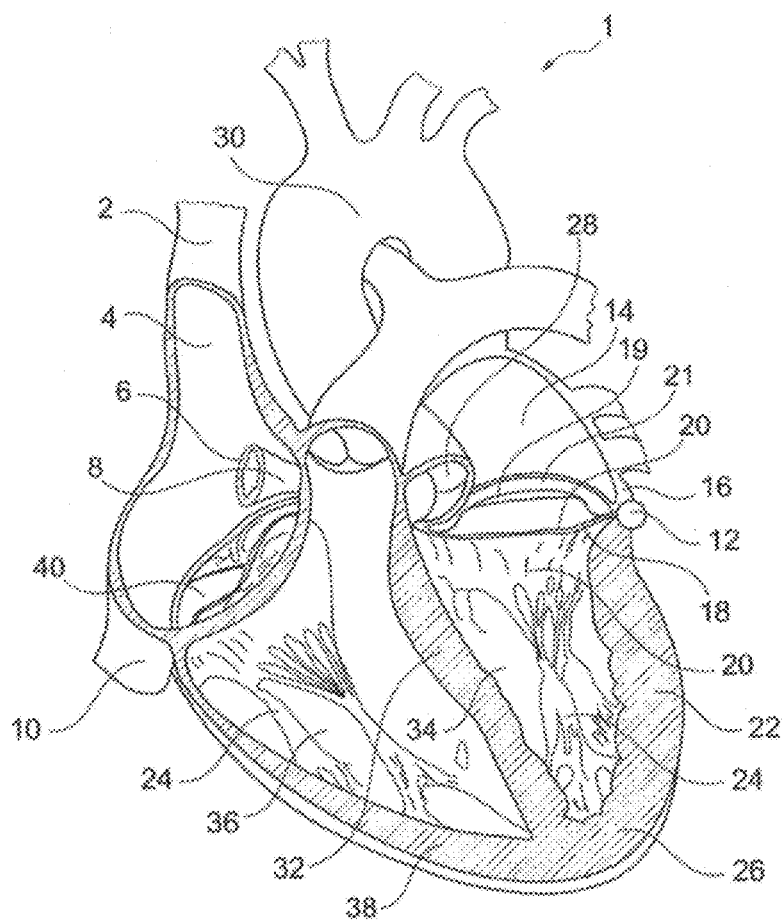
FIG. 1 is a schematic illustration of a heart and its anatomical structures, partly cross-sectional schematic illustration of a human heart depicting structures that are involved.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

FIG. 1 depicts the anatomical structures of the heart 1, of which at least some are involved in embodiments of the invention, 2 is the Superior Vena Cava (SVC), 4 is the right atrium (RA), 6 is the Coronary Sinus (CS) ostium, 8 is the CS first part, 10 is the Inferior Vena Cava (IVC), 12 is the Great Cardiac Vein (GCV) at the level of the mitral valve (MV) annulus 18, 14 is the Left Atrium cavity (LA), 16 is the LA wall, 19 is the whole mitral valve, 20 is the anterior leaflet and 21 is the posterior leaflet of the mitral valve, 22 is the Left Ventricular (LV) muscular wall, 24 are the papillary muscles connected to the chordae, 26 is the apex of the left ventricle, 28 is the aortic valve, 30 the aorta ascendens, 32 the inter-ventricular muscular septum, 34 the left ventricular cavity and 36 the right ventricular cavity, 38 is the right ventricular muscular wall and 40 is the tricuspid valve.

Figure 2:
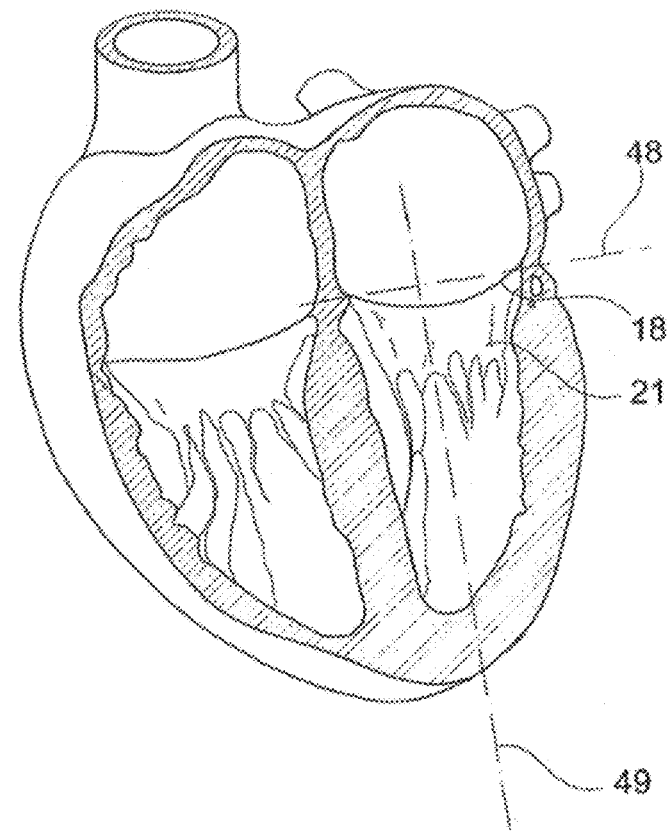
FIG. 2 is a schematic illustration of a heart and its related cardiac valves as well as the cardiac axis.

FIG. 2 shows the cardiac valve plane 48 in relation to the cardiac axis 49 of the left ventricle.

Figure 4A:
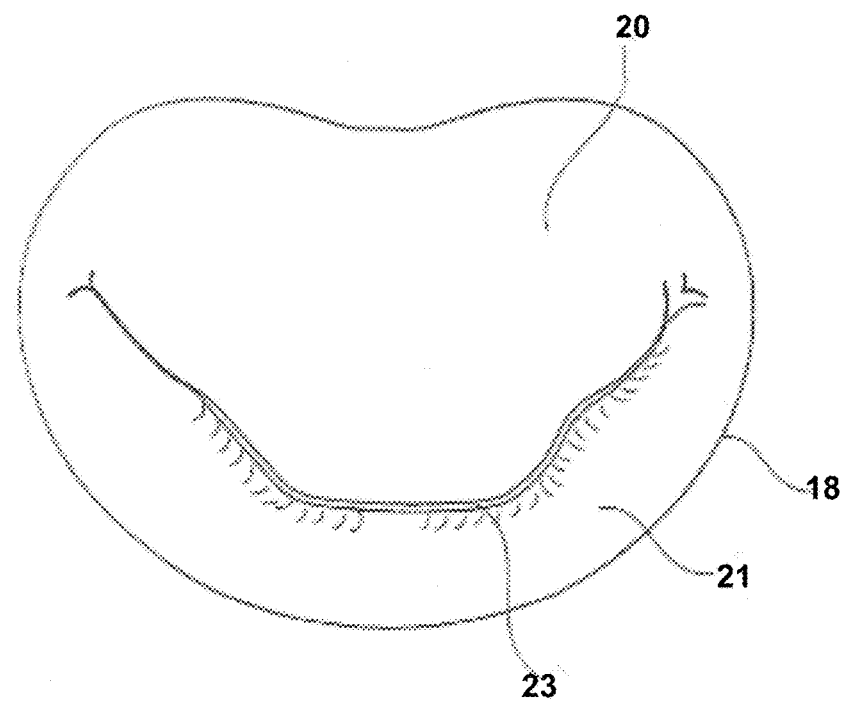
FIG. 4a-d are schematic illustrations that show a mitral valve and the placement of a mitral valve annulus anchor with one or more stabilizing coupling units.

In an example an implantable medical device is provided that includes a flexible anchor unit 100 including an annuloplasty implant. The annuloplasty implant is, when implanted, permanently anchored at an annulus of a cardiac valve of a patient. The medical device further includes at least one locking unit 300 and at least one coupling unit 200 for connecting the anchor unit 100 to the at least one locking unit 300. The coupling unit 200 preferably includes at least one lockable arm, and has a first end portion and a second end portion. The first end portion is connectable to the anchor unit 100, and when implanted connected thereto. The second end portion includes the locking unit 300. In this manner, such at least a part of a shape of the anchor unit 100 is fixed when the anchor unit 100, coupling unit 200 and locking unit 300 are connected for stabilizing the anchor unit 100 at the annulus. See for instance examples illustrated in FIGS. 4a), b), c), and d) and the corresponding description. The annulus can be annulus tissue or other unit, e.g. previously implanted other device/implant.

In another example, an implantable medical device is provided that includes an anchor unit 100 permanently anchored at a cardiac valve of a patient, when implanted. The device further includes at least one locking unit 300 for fixation of tissue of the cardiac valve, and at least one coupling unit 200 for connecting the anchor unit 100 to at least one locking unit 300. The coupling unit 200 has a first end portion. The coupling unit 200 is, when implanted, connected at the first end portion to the anchor unit 100 and connected remote of the first end portion to the tissue of the cardiac valve by the locking unit 300. See for instance examples illustrated in FIGS. 5a) and b) and the corresponding description.

In another example, a system is provided. The system includes an implantable medical device including an anchor unit 100 to be permanently anchored at a cardiac valve of a patient. The device includes at least one locking unit 300, and at least one coupling unit 200 for connecting the anchor unit 100 to at least one locking unit 300. The coupling unit 200 is preferably at least one arm and has a first end portion and a second end portion. The first end portion is connectable to the anchor unit 100, and the second end portion includes the locking unit 300. The system further includes a driving unit 500, for example a driving unit of a cardiac assist device, which is releasably or permanently connected to the at least one coupling unit 200, at the second end portion by the locking unit 300. See for instance an example illustrated in FIG. 6 and the corresponding description.

In another example, a system is provided. The system includes an implantable medical device including an anchor unit 100 configured to be permanently anchored at a cardiac valve of a patient. The system includes at least one locking unit 300. The system includes at least one coupling unit 200 for connecting the anchor unit 100 to at least one locking unit 300. The coupling unit 200 is preferably at least one arm. The coupling unit 200 has a first end portion and a second end portion, wherein the first end portion is connectable to the anchor unit 100. The second end portion preferably includes the locking unit 300. The system further includes a further unit, such as a cardiac valve replacement or repair unit 600. The anchor unit 100 is connected to the further unit, such as a cardiac valve replacement or repair unit 600, preferably being connected to each other via said at least one coupling unit 200. See for instance examples illustrated in FIG. 7a), b), and c), FIG. 8a), b), c), d), e), f), and g) and the corresponding description.

In an example an implantable medical device is provided, which includes an anchor unit 100 that is permanently anchored at a cardiac valve of a patient, when implanted. The device further includes at least one locking unit 300. The locking unit 300 is preferably providing fixation of tissue of the cardiac valve. Alternatively, or in addition, the locking unit 300 is providing fixation of at least a part of a shape of the anchor unit 100. The device further includes at least one coupling unit 200 for connecting the anchor unit 100 to at least one locking unit 300. The coupling unit 200 has a first end portion and a second end portion, wherein the first end portion is connectable to the anchor unit 100, and when implanted connected thereto. The second end portion includes in some embodiments the locking unit 300.

Figure 3A:
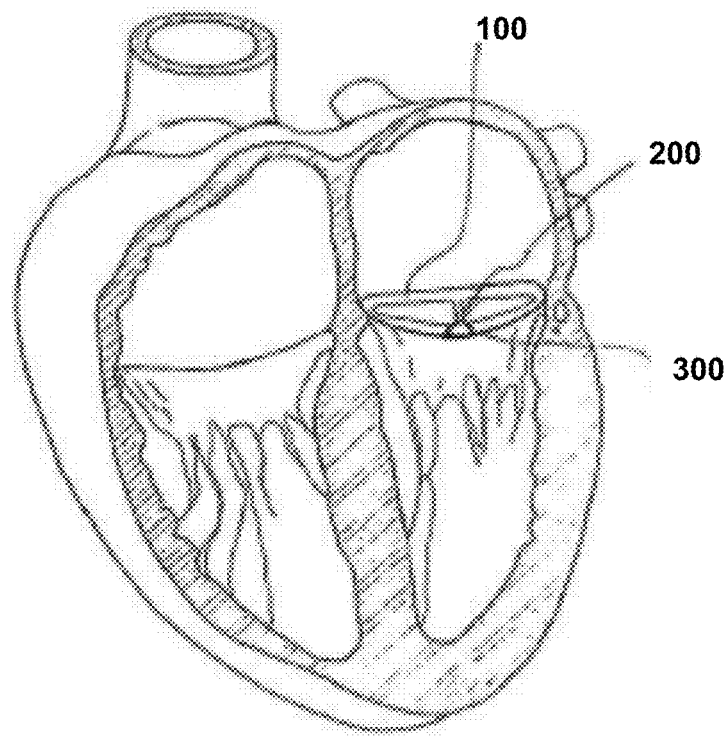
FIG. 3a-b are cross section view of the heart illustrating an anchor unit anchored at the mitral valve and the tricuspid valve respectively.
Figure 3B:
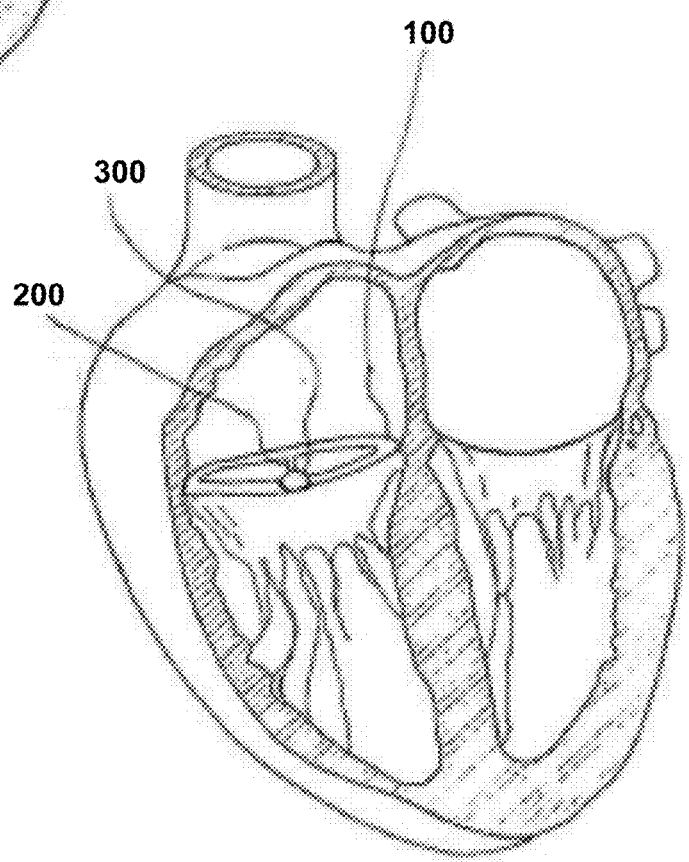

The cardiac valve is preferable one of the valves between an atrium and a ventricle, i.e. the mitral valve or the tricuspid valve. A locking unit 300, a coupling unit 200, and the anchor unit 100 that is anchored at the mitral valve and/or the tricuspid valve which are illustrated in FIG. 3a) and FIG. 3b), respectively. The cardiac valve may also be one of the aortic valve or the pulmonary valve, where the valve comprises three valve leaflets as in the tricuspid valve illustrated in FIG. 8f) and FIG. 8g). Some of these arrangements can be present at the same time at different valves, respectively, depending on the clinical needs and therapy requirements of a specific patient.

An anchor unit 100 is for instance at least partially loop shaped or horse shoe shaped and is preferably flexible or partly flexible or flexible in one dimension and rigid in another dimension. The anchor unit 100 is anchored at an annulus of the cardiac valve, in a plane of the cardiac valve perpendicular to a longitudinal axis of the heart, in the case of the mitral valve see FIG. 2 for illustration.

A suitable anchor unit 100 in form of a chain annuloplasty ring, suitable for all aspects of the present disclosure, i.e. to include or attach coupling unit(s) e.g. for stabilization of the ring, connection to tissue fixation units, connection of a cardiac assist device or a valve replacement/repair device, are described in concurrently filed patent application of the same applicant with the title "A chain annuloplasty ring, delivery system and related methods". This patent application is incorporated herein by reference in its entirety for all purposes. In particular the disclosure of a chain annuloplasty ring with chain segments, in particular for synergistic treatment of valve regurgitation, preferably in addition to stabilization purposes, and/or preferably in addition to the below described "clipping" of valve tissue, when connected to the presently herein described examples of an anchor unit, then in form of a chain annuloplasty ring. The ring does not necessarily need to foreshorten for an annuloplasty, but may as well simply serve as an anchor unit, see e.g. FIG. 15 and related text of the concurrently filed patent application.

The anchor unit 100 can be previously implanted and in place at the annulus of the cardiac valve and ready for attaching a first end of a coupling unit 200. Alternatively, the anchor unit 100 can be integrated with a coupling unit 200 and implanted together in the same procedure.

The anchor unit 100 can be designed for annuloplasty and can be such as an annuloplasty implant, annuloplasty ring, or annuloplasty loop, which can be open partial, loop shaped, horse shoe shaped, and/or C-shaped, D-shaped etc.

The anchor unit 100 is anchored to the annulus tissue at the cardiac valve with, e.g. a screw, hook, tab, suture 60, staple, etc.

The anchor unit 100 may also be such as a coronary sinus implant, e.g. in the form of a stent, implanted near the annulus of the cardiac valve. The coupling unit may in examples like this penetrate cardiac tissue between their ends.

The coupling unit 200 is in examples configured to be attached or connected at the first end portion to the anchor unit 100, e.g. connected by a clamp, threaded, integral/monolithic, weld, screw, rivet, hinge, etc. Alternatively, the coupling unit 200 can at its first end portion be formed as a monolithically integrated piece of the anchor unit (it may in examples still be arranged to flex or pivot as long as the second end is not attached or affixed, such that transluminal delivery is facilitated). In most examples, the coupling unit is along its length rigid, like a rod or strut element, see also more details given below. However, it may have different shapes, e.g. during delivery and upon installation/implantation, for instance being of a shape memory material and different set shapes as needed.

In an example, the anchor unit 100 is a flexible anchor unit, such as a chain annuloplasty ring. The at least one coupling unit 200 and the fixation includes stabilizing the anchor unit 100 when the coupling unit 200 is connected to the anchor unit 100 and locked by the locking unit 300. Flexibility of the anchor unit 100, before being stabilized or locked in shape, is advantageous as it can adapt to specific anatomical topographies, and then to be locked in place, e.g. for preventing a widening of the anchor unit 100.

Figure 4B:
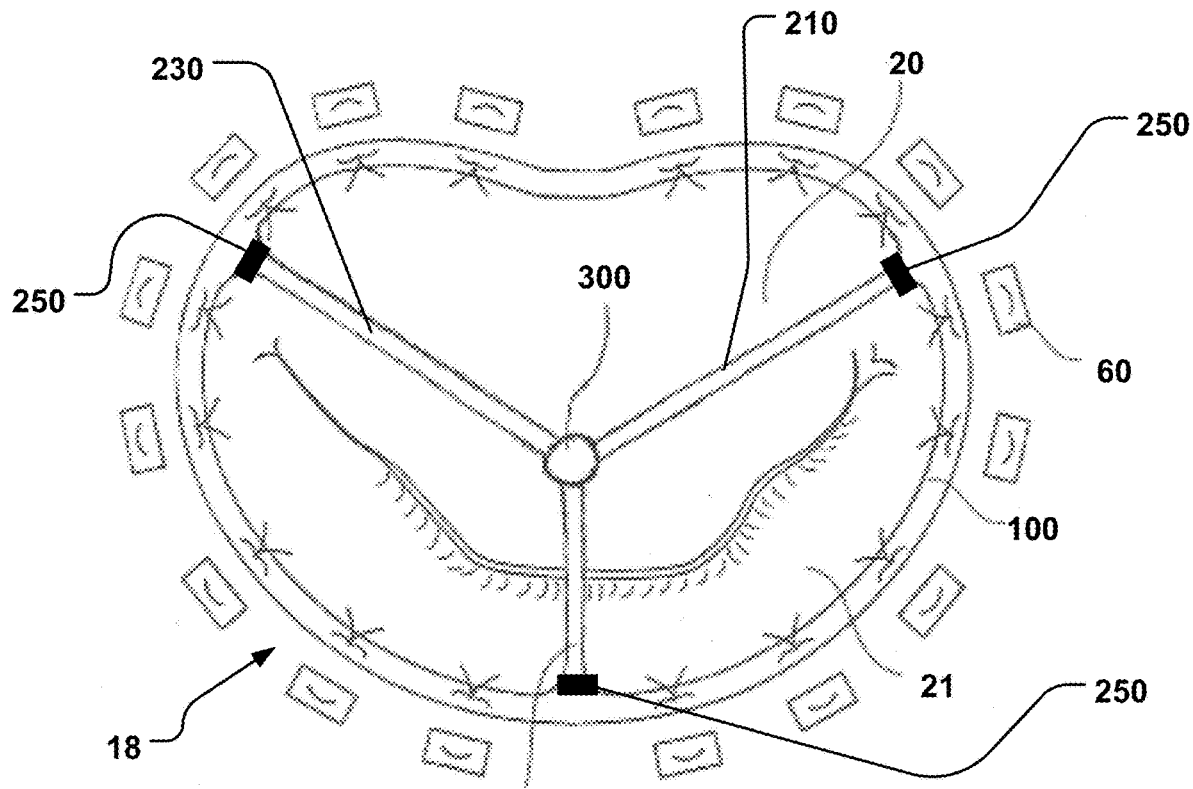
Figure 4C:
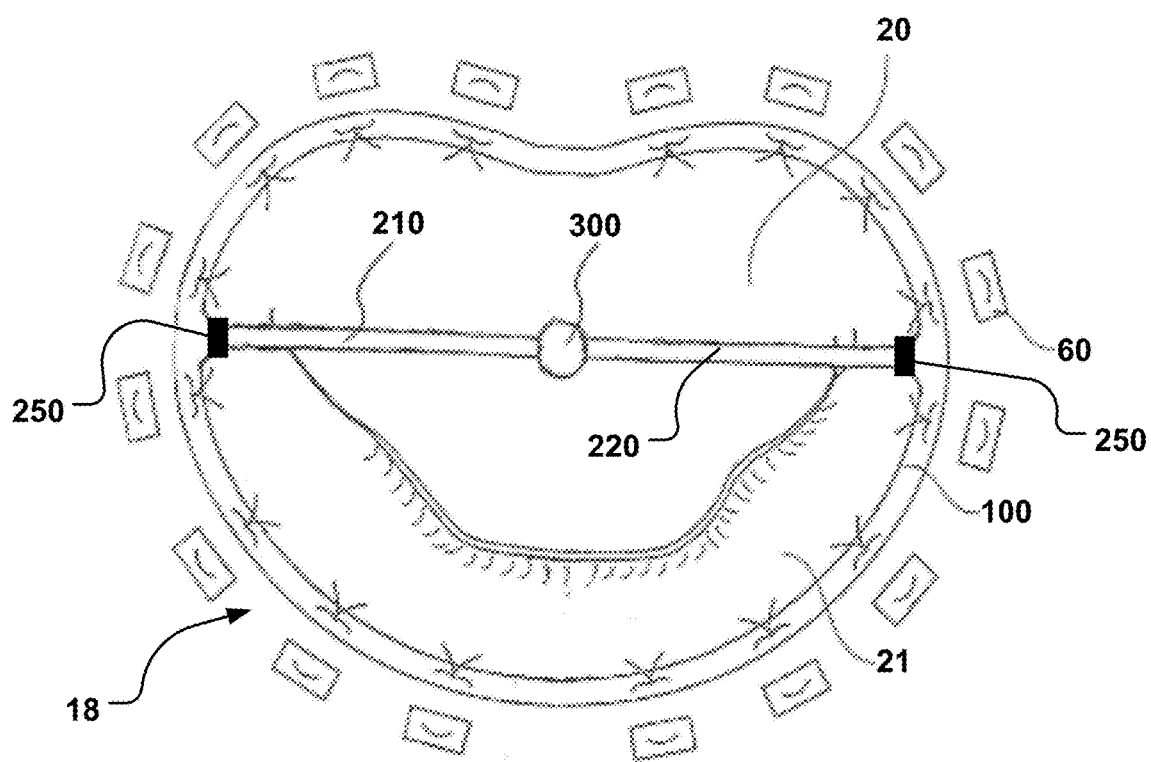

The coupling unit (first coupling unit 210) is for instance locked to at least one other coupling unit (second coupling unit 220), for instance in a star shape formation as in FIG. 4*b*) or in a line shape formation as in FIG. 4*c*).

Figure 4D:
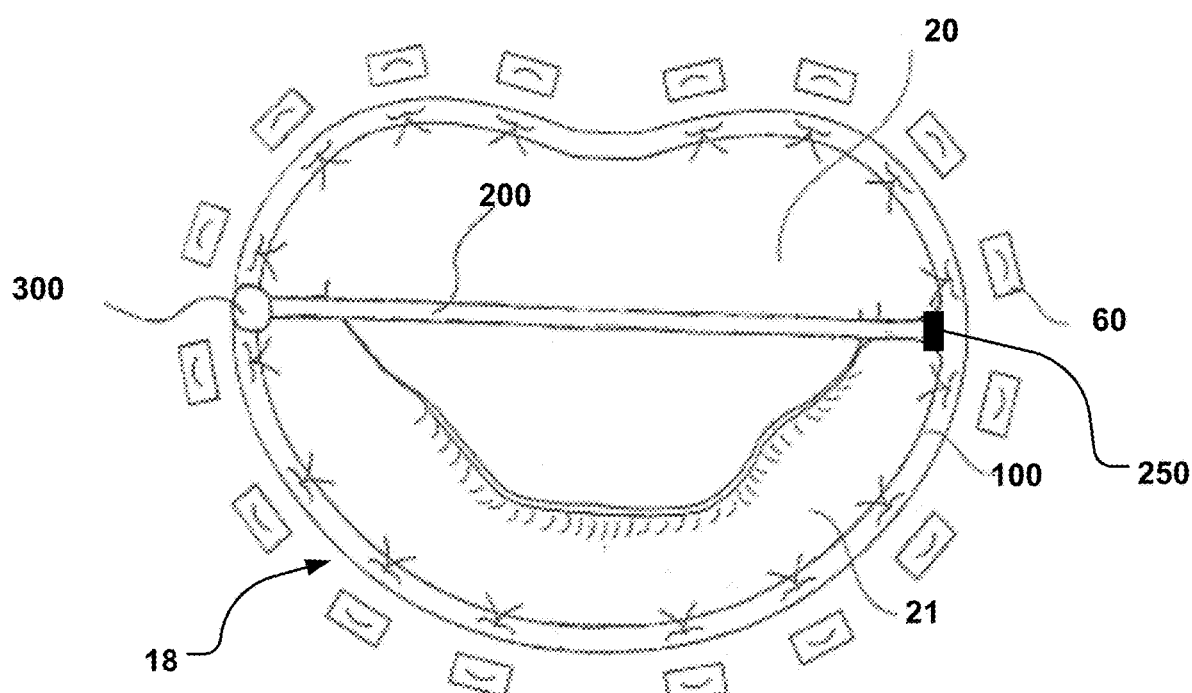

At least one coupling unit 200 is alternatively, or in addition at its second end portion locked to a portion of the anchor unit 100 remote of the first end position at the anchor unit 100 as in FIG. 4*d*).

Combinations can be provided as needed for any desired stabilization of an anchor unit 100.

A coupling unit 200 is for instance an elongate element, such as an arm, a lever, a pin, a rod, a stick, a strut, a pipe, a wire, a cable, a thread, a nitinol thread/wire, etc.

The length of the coupling unit 200 can either be fixed or adjustable. It can be adjustable before locking. The length can be adjusted as desired and then fixed to a permanent length in suitable ways, e.g. screws, threads, splints, etc. The length can also be non-reversibly adjustable, i.e. only in one direction before locking to a permanent length.

The coupling unit 200 is preferably straight, but in other examples it may be curved.

One or several coupling units 200 may be used were one or several coupling units 200 are locked be the locking unit 300, e.g. the locking of one coupling unit 200 is illustrated in FIG. 4*d*), the locking of two coupling units (210, 220) are illustrated in FIG. 4*c*), and the locking of three coupling units (210, 220, 230) are illustrated in FIG. 4*b*) (star shape formation).

The coupling units 200 can for instance extend with their distal end portion located on the atrial side of the cardiac valve plane, such as looped back towards the apex, or in the cardiac valve plane, or towards a center of the coaptation line of the cardiac valve leaflets.

The flexible anchor unit 100 can for instance be made of several links and when the coupling unit 200 is fixated by the locking unit 300, the links in the anchor unit 100 are locked which stabilizes the anchor unit 100.

"Stabilizing" as used in the present context means to make stable, steadfast, keep permanently in a shape.

An anchor unit 100 without a coupling unit 200 and locking unit 300 can become more flexible over time, either the whole anchor unit 100 or just some parts of it. Thus, a coupling unit 200 fixated with a locking unit 300 stabilizes the anchor unit 100 and will prevent the unwanted flexibility and thus widening to occur. A coupling unit 200 and a locking unit 300 can also stabilize a previously implanted anchor unit 100, and thus correct an unwanted flexibility. The prevention and/or the correction of the unwanted flexibility can either be with respect to the whole anchor unit 100 or just some parts of the anchor unit 100 where at least part of the shape of the anchor unit 100 is locked by means of one or more coupling unit(s) 200.

The stabilization of the anchor unit 100 and/or the stiffening of the anchor unit 100 can thus prolong durability and life expectancy of the anchor unit 100. In the case of the anchor unit 100 being an annuloplasty ring, the stabilization with the coupling unit 200 and locking unit 300 can prevent and/or correct the annuloplasty ring from leakage caused by an unwanted widening and/or growing and/or enlargement of the ring. Such leakage can include paravalvular leakage and regurgitation.

The coupling unit 200 includes for instance at least one lockable arm for the fixation of the shape of the anchor unit 100. In this manner, a second end portion is locked to the anchor unit 100 at a different position than the first end portion for stabilizing the anchor unit 100, preferably by a locking unit 300. The locking is in the example done remote of the first end portion as is illustrated in FIG. 4*d*).

Figure 5A:
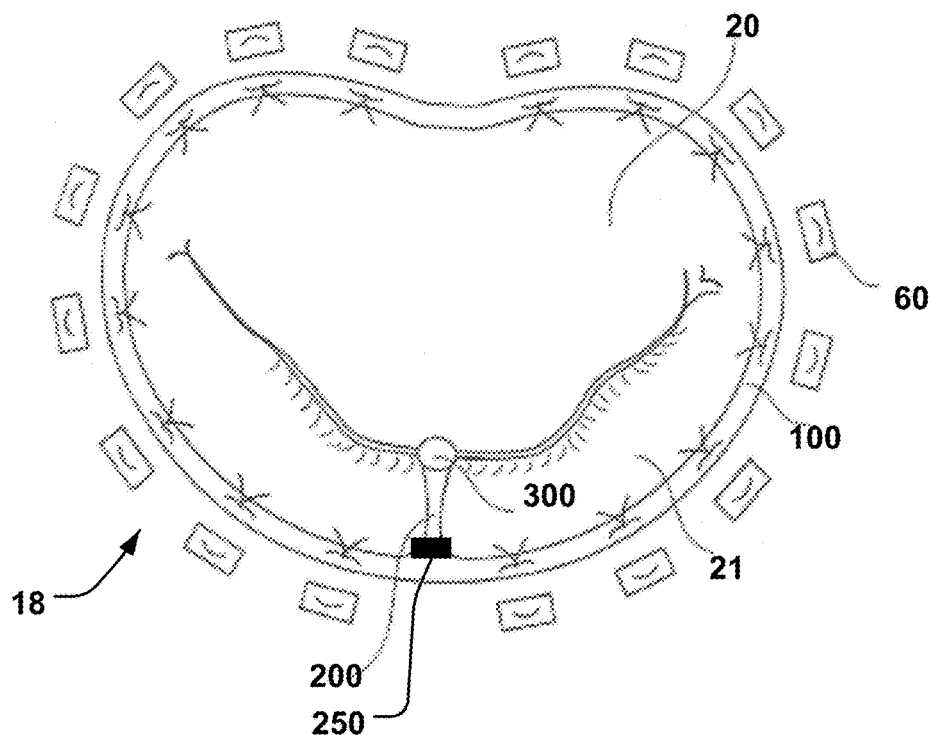
FIG. 5a is a schematic illustration that show a mitral valve and the placement of a mitral valve annulus anchor and a locking unit for fixating cardiac valve tissue.
Figure 5B:
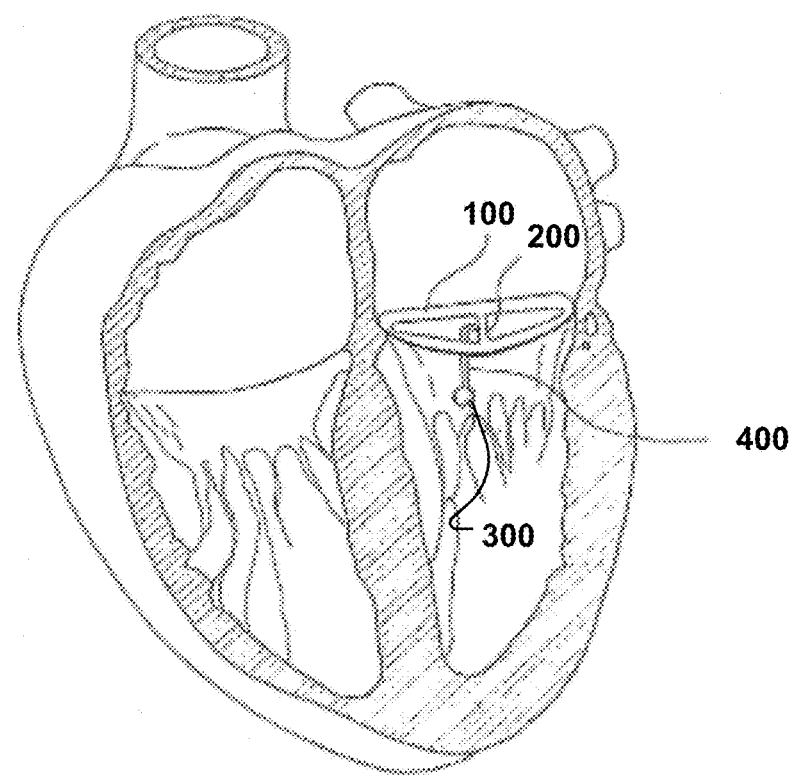
FIG. 5b is a cross section view of a heart illustrating an anchor unit anchored at the mitral valve, an extension unit and a locking unit for fixating cardiac valve tissue.

In examples, the coupling unit 200 includes at least one preferably lockable arm connectable at a first end to the anchor unit 100 and connectable remote of the first end to at least one leaflet of the valve for the fixation of tissue of the cardiac valve as illustrated in FIG. 5*a*) and FIG. 5*b*).

A coupling unit 200 is for instance elongate as an arm, a lever, a pin, a rod, a stick, a pipe, with at least one locking unit 300 at a second end portion or e.g. along the rod for grabbing cardiac valve tissue. The coupling unit 200 being configured to be attached at the first end portion to the anchor unit 100, e.g. connected by a clamp, threaded, integral/monolithic, weld, screw, rivet, hinge, for instance as a lockable arm. Alternatively the arm is locked at the second end point and thereby also locking the first end too. The length of the coupling unit 200 can either be fixed or adjustable.

The coupling unit 200 is configured to be attached at the second end portion to the locking unit 300. Suitable attachment may for instance be provided by a clamp, threaded, integral/monolithic, weld, screw, rivet, hinge, etc. The attachment is configured to be arranged remote of the first end portion, such as in a ventricular chamber, at leaflets, chordae, ventricular muscle tissue or in an atrium.

The locking unit 300 is in examples configured to be a tissue securing component for example being a suture having a looped portion, a clip, a clamp adapted to be crimped around one leaflet and/or chordae, or a clip/clamp adapted to be crimped around two or more leaflets and/or chordae, see some examples in FIG. 5*a*) and *b*). The fixation of tissue of the cardiac valve achieved by the locking unit 300 is for instance a cardiac valve clip and is configured to be attached at any cardiac valve, thus the locking unit 300 can act as a mitral clip, tricuspid clip, aortic clip, or pulmonary clip.

The locking unit 300 is in such tissue securing applications configured to correct leakage of a cardiac valve. The leakage can be corrected by attaching the locking unit 300 at any suitable fixation position and place of the leaflet and/or chordae of the cardiac valve. A range of movement of the leaflets is thus controlled or limited mechanically by the attached locking unit in order to improve sealing function of the leaflets and the valve in general. A pinching together of several leaflets can in examples likewise be provided at selected positions of the leaflets/chordae or related anatomical structures. Examples of suitable locking units in form of tissue clips that can be implemented with the coupling units disclosed herein are for instance disclosed in WO2006/047709A2, WO2006/086434A1, WO2006/116558A2, WO2013/039810A1, WO2017/015288A2, WO2018/102310A1, or similar, which all are incorporated herein by reference for all purposes.

Multiple locking units 300 (with multiple attachments) can be provided in some examples to correct multiple leakages at different places of the cardiac valve.

The locking unit 300 can provide improved fixation of cardiac valve tissue by a cardiac clip attached to e.g. a coupling unit 200 and/or an anchor unit 100 e.g. a stabilized annuloplasty implant. The locking unit 300 is in some examples configured to be attached to only one leaflet, either with one attachment (e.g. a clip) locked to the leaflet or with more than one attachments locked to the leaflet at the same or at different positions. The locking unit 300 is in other examples also configured to be attached to more than one leaflet, either with one attachment locked to the leaflets or with more than one attachments locked to the leaflets at the same or at different positions of the valve leaflets, chordae or other related anatomical valve structures.

In examples of the device, a driving unit 500, such as of a cardiac assist device, is connectable to the at least one coupling unit 200. The connection of such driving unit 500 is for instance made at the second end portion. The locking unit 300 is preferably connecting the driving unit 500 in a lockable manner to the device. The coupling unit 200 is preferably at least one arm. See for instance FIGS. 5 and 6.

The driving unit 500 can be a cardiac assist device e.g. designed for pushing and/or pulling of the cardiac valve plane along the cardiac longitudinal axis. Such cardiac assist device 500 assists the natural motion of the cardiac valve plane, thus improving the movement of the cardiac valve plane and enhancing the cardiac function. The pushing and/or pulling of a cardiac valve plane along the cardiac longitudinal axis can be done by e.g. pushing and/or pulling the anchor unit 100, since the anchor unit 100 is permanently anchored at a cardiac valve of a patient. Examples of such cardiac assist devices are disclosed in international patent applications of the same inventor as the present application with publications numbers WO2011/119101A1 or WO2011/119100A1, which both are incorporated herein in their entirety for all purposes. The presently described anchor unit 100 is in examples attached to the mitral valve plane and its movement is assisted during the cardiac cycle, preferably substantially along a cardiac long axis. Other cardiac valves may thus likewise be assisted for improving cardiac function, e.g. the tricuspid valve.

The coupling unit 200 enables the option to enhance an implantable medical device by connection of, for instance at the second end point of the coupling unit 200, a driving unit 500, such as a cardiac assist device, at the time of implantation of the medical device and/or at a later stage if needed. The anchor unit 100 of the medical device can be an annuloplasty ring with the purpose to stop a leakage in a cardiac valve. It is well known that mitral regurgitation is one of the most prevalent valve diseases, as well as that mitral regurgitation is common in advanced heart failure patients in need of cardiac assist. Thus if the anchor unit 100 is an annuloplasty ring, at the time of implantation, it would be beneficial to connect a cardiac assist device 500 to the coupling unit 200 of the medical device. It may also be the case that patients suffering from mitral regurgitation may develop a more advanced heart failure with time, making these patients in need of a future cardiac assist. For these patients, the leakage can be stopped with an annuloplasty ring as an anchor unit 100 of the medical device, but the connection of a cardiac assist device 500 to the coupling unit 200 can be done at a later stage when the cardiac assist is needed.

The locking unit 300 can be configured to obtain a secure locking of the cardiac assist device 500 to the medical device and/or the anchor unit 100. In this manner, a synergetic solution is provided that both can stabilize an anchor unit and prevent widening of the anchor unit 100 over time, and also facilitate a cardiac assist. A cardiac assist device can be implanted and attached to the anchor unit at a later point in time than implanting the anchor unit 100 itself. The cardiac assist device 500 can push and/or pull the cardiac valve plane and/or the anchor unit 100 during every heartbeat, i.e. the pushing and/or pulling may be done once every second, or equivalently, more than thousand times every hour and more than million times every month. Thus, a secure locking of the cardiac assist device 500 to the medical device and/or the anchor unit 100 is important in order to have a robust and functional cardiac assist device 500. Examples of the locking unit 300 can provide such a reliable locking of the cardiac assist device 500 to the medical device and/or the anchor unit 100.

The coupling unit 200 is preferably at least one arm, but can for instance also be one or more of, a lever, a pin, a rod, a stick, or a pipe. The driving unit 500 is connectable to the at least one coupling unit 200, where the for instance at least one arm of the coupling unit 200 can extend inwardly towards a center of the loop in the cardiac valve plane, or towards a center of the coaptation line of the cardiac valve leaflets, or crossing the cardiac valve plane towards the apex of the heart which may or may not enter into the ventricle by various means. The length of the coupling unit 200 can either be fixed or adjustable.

The anchor unit 100 is permanently anchored at a cardiac valve of a patient, thus the medical device can provide the cardiac assist device 500 with an advantageous natural anchor for the pushing and/or pulling of the cardiac valve plane. The anchor can be a stabilized anchor. The locking unit 300 can be configured to obtain a reliable and secure locking of the cardiac assist device 500 to the medical device and/or the anchor unit 100 for repeatable pushing and/or pulling. The coupling unit 200 enables the option to enhance an implantable medical device by connection of, for instance at the second end point of the coupling unit 200, a cardiac assist device 500 at the time of implantation of the medical device or at a later stage if needed. Patients suffering from mitral regurgitation and/or advanced heart failure in need of cardiac assist can be treated with the implantable medical device, if the anchor unit 100 is an annuloplasty ring and/or a cardiac assist device 500 is connected to the coupling unit 200 of the medical device. In this way, two different heart failure conditions may be treated with the same implantable medical device.

In examples, the locking unit 300 includes an attachment element for releasably connecting the cardiac assist device 500 to the anchor unit 100.

In examples, the coupling unit 200 includes along its length at least one freely pivoting and/or rotating joint. The joint may be integrated into the attachment element and the pivot function be activated upon coupling together.

The attachment element included in the locking unit 300 is for instance a magnetic/magnet coupling, a threaded attachment unit, a bayonet coupling/connector, a clamp, cable ties, tie raps, zip ties, ratchet type, a ball connector, a ball chain connector, a grip coupling, or a grooved coupling. Thus, the attachment element can be of magnetic, mechanical, and electrical nature, or any combination thereof.

The attachment element is in examples configured for a releasable connection between the cardiac assist device 500 and the anchor unit 100. The releasable connection can be used if a cardiac assist is not needed at time of implantation, but a connection of a cardiac assist device 500 to the coupling unit 200 is rather needed at a later stage. Thus, the releasable connection enables the attachment to be done in a later procedure if disconnection of the cardiac assist is needed. Another particular advantage is that the releasable connection also enables the cardiac assist device 500 to easily be exchanged, e.g. in case of a technical failure and the cardiac assist device 500 need to be replaced.

The locking unit 300 can be configured to be bendable and/or moveable in such a manner that any part of the cardiac assist device 500 may bend and/or move freely with respect to the anchor unit 100 and/or the coupling unit 200. After implantation of a medical device, where a bending of the locking unit 300 is not possible due to a rigid connection between the cardiac assist device 500 and the anchor unit 100 and/or the coupling unit 200, patients may experience pain and discomfort, internal bleedings may occur, and in extreme cases there may be an obstruction of the proper function of the cardiac assist device 500. Thus, it is of particular advantage to have a bendable and/or moveable locking unit 300 in order to avoid a straight rigid and/or solid connection between the cardiac assist device 500 and the anchor unit 100 and/or the coupling unit 200. Several occasions may occur when a bendable and/or moveable locking unit 300 is needed, e.g. when the patient bends, moves, twists, turns, and/or stretches the torso and/or the thorax, and may also occur e.g. during heavy breathing, coughing, and/or sneezing. The free movement of a bendable locking unit 300 may for instance be obtained with at least one locking unit 300, which for instance includes a magnetic coupling (e.g. comprising two magnetic balls), and/or a mechanical coupling (e.g. in the form of a ball connector, hinge, pivot, flex joint, break safe superelastic material, etc.). Such couplings may ensure a bendable and/or moveable locking unit in order to allow the cardiac assist device 500 to bend and/or move freely (such as freely pivoting and/or rotating) with respect to the anchor unit 100 and/or the coupling unit 200, see FIG. 6 for an illustration.

The medical device includes in examples a plurality of coupling units 200. The first end portion of each of the coupling units 200 include an attachment unit pivotably connecting the coupling unit 200 to different positions at the anchor unit 100. The second end portion of the coupling units 200 is connected to each other by at least one of the locking units 300.

In more detail, the second end portion of the coupling units 200 is in certain examples connected to each other by at least one locking unit for instance comprising a suture, clip, clamp, magnetic/magnet coupling, threaded attachment unit, bayonet coupling/connector, cable ties, tie raps, zip ties, ratchet type, ball connector, ball chain connector, grip coupling, and/or grooved coupling. The locking unit 300 can also comprise a plug, tap, nail, bolt, screw, and/or rivet, preferably when a mating recess, e.g. a through hole is included in the second end portion of the coupling units 200. In one example, all the through holes included in the second end portion of the coupling units 200 are aligned when the coupling units 200 are pulled together (e.g. in the shape of a star or a line, see FIG. 4b) and FIG. 4c) for illustration), and all the coupling units 200 are connected and locked to each other by inserting a securing unit, such as a plug, tap, nail, bolt, screw, or rivet, through the holes.

In another example, the second end portion of the coupling unit 200 includes different elements and parts of an interlocking system, and when brought together they form and construct the locking unit 300 for interlocking the coupling units to each other. For instance, in the case of three coupling units 200 as in FIG. 4b), the second end portion of the first coupling unit 210 may include a hole, the second end portion of the second coupling unit 220 may include a screw, and the second end portion of the third coupling unit 230 may include a nut, and when brought together, the screw goes through the hole and is finally locked by the nut. In another example, the second end portion of the coupling units 200 may include magnets, and when brought together, the alignment of the magnets cause the locking of the coupling units 200.

The attachment unit, pivotably connecting the coupling unit 200 to different positions at the anchor unit 100, included at the first end portion of each of the coupling units 200 enables a compact delivery configuration, since the coupling units 200 may e.g. be folded over, under, and/or along the anchor unit 100 at the time of delivery through a catheter.

The plurality of coupling units 200 included in the medical device enables various configurations and formations, which enables the medical device to be advantageously adaptive to different patient geometries and anatomies.

The coupling unit 200 includes in examples an extension unit 400 that extends from an annulus of the cardiac valve towards the apex of the heart.

The extension unit 400 is for instance configured to be an arm, a lever, a pin, a rod, a stick, a pipe, see FIG. 5b. The extension unit 400 has a proximal region, e.g. close to the annulus of the cardiac valve, and a distal end region, e.g. close to the apex of the heart. The extension unit 400 may also be more than one arm, lever, pin, rod, stick, pipe, with the same and/or different lengths, and may also for instance be one rod in the proximal region and then the rod is divided or branches into two or more rods in the distal end region. The length of the extension unit 400 can be short and may only extend to right below the annulus of the cardiac valve, and can be long and may extend all the way down to the apex of the heart, and can also be all the lengths in between. In another example, the extension unit 400 can extend into the atrium. The length of the extension unit 400 can either be fixed or adjustable.

The coupling unit 200 can include an extension unit 400 as e.g. a rod that extends perpendicular to the cardiac valve plane, see FIG. 5b) and FIG. 6. The coupling unit 200 can also include an extension unit 400 as e.g. a rod that extends through and crosses the center of the coaptation line of the leaflets of the cardiac valve. The extension unit 400 can have the same thickness all the way, but can also have different thickness at different longitudinal positions. The extension unit 400 can e.g. be thinner at the point where it crosses the coaptation line of the leaflets of the cardiac valve in order to have minimal impact on the closing of the valve leaflets, or can e.g. be thicker at the point where it crosses the coaptation line of the leaflets of the cardiac valve in order to fill out for an insufficient closing of the valve leaflets.

The extension unit 400 can have a locking unit 300 in the proximal region, and/or in the distal end region. For instance, the extension unit 400 can have the locking unit 300 in the distal end region, and the locking unit 300 can be a clip for locking the distal end region of the extension unit 400 to the leaflets of the cardiac valve, and/or the locking unit 300 can be locked to a cardiac assist device 500. The locking unit 300 in the distal end region of the extension unit 400 can also include an attachment element for releasably connecting the cardiac assist device 500 and/or the cardiac valve clip.

The extension unit 400 can thus advantageously provide locking, coupling, attachment, and/or releasably connection to other units at any place and position inside the heart during the implantation of the medical device or at a later time after the implantation of the medical device. Thus, the extension unit 400 enables and facilitates the option to enhance an implantable medical device with e.g. a cardiac valve clip and/or a cardiac assist device 500 at the time of implantation and/or at a later stage if needed. In this way, the extension unit 400 that extends from an annulus of the cardiac valve towards the apex of the heart provides a flexible and modular approach to enhance the implantable medical device in a beneficial manner.

The extension unit 400 has in examples the locking unit 300 arranged to fixate at least one leaflet and/or chordae to the extension unit 400 to limit a range of motion thereof during the cardiac cycle.

The locking unit 300 and the extension unit 400 are configured to correct leakage of a cardiac valve. The extension unit 400 is configured to position the locking unit 300 at any position inside the heart e.g. in order to facilitate the correction of the leakage at any position and place of the leaflet and/or chordae of the cardiac valve. The extension unit 400 is in examples configured to connect multiple locking units 300 (with multiple attachments) in order to correct multiple leakages at different places of the cardiac valve.

The locking unit 300 and the extension unit 400 can provide improved fixation of cardiac valve tissue by a cardiac clip attached to the extension unit 400 and/or an anchor unit 100 e.g. a stabilized annuloplasty implant.

The locking unit 300 is in examples configured to be attached to the extension unit 400 and to only one leaflet, either with one attachment (e.g. one clip) locked to the extension unit 400 and the leaflet or with more than one attachments locked to the extension unit 400 and the leaflet at the same or at different positions.

The locking unit 300 is alternatively or in addition configured to be attached to the extension unit 400 and to more than one leaflet, either with one attachment locked to the extension unit 400 and the leaflets or with more than one attachments locked to the extension unit 400 and the leaflets at the same or at different positions.

The locking unit 300 is alternatively or in addition configured to be freely attached to the extension unit 400 and locked to more than one leaflet, either with one attachment locked to the leaflets or with more than one attachments locked to the leaflets at the same or at different positions.

In this way, the locking unit 300 is attachable to more than one leaflets which are locked to each other, and at the same time the locking unit 300 is attached to the extension unit 400 but the locking unit 300 with the locked leaflets is allowed to move freely along the extension unit 400, etc.

The locking unit 300 is in particular examples a device for gathering tissue of cardiac valve leaflet tissue of the cardiac valve and adapted to be attached to the extension unit 400 and the leaflet tissue. The locking unit 300 for gathering tissue of the cardiac valve leaflets can be located towards the center of the anchor unit 100 in the valve plane, or towards the center of the coaptation line of the leaflets of the cardiac valve as illustrated in FIG. 5a), or below the cardiac valve plane attached to an extension unit 400 as illustrated in FIG. 5b).

The locking unit 300 can in examples be a tissue securing component adapted to be applied to the captured tissue to hold the captured tissue in the gathered configuration. In examples, the locking unit 300 includes the tissue securing component for example being a suture 60 having a looped portion, a clip, a clamp adapted to be crimped around one or more leaflets and/or the extension unit 400.

In examples, the first end of the coupling unit 200 includes an attachment unit 250 for attaching the first end to the anchor unit 100.

The attachment unit 250, included in the first end of the coupling unit 200 e.g. illustrated in FIG. 4b) and FIG. 4c), for instance comprises a suture, clip, clamp, plug, tap, nail, bolt, screw, rivet, magnetic/magnet coupling, threaded attachment unit, bayonet coupling/connector, cable ties, tie raps, zip ties, ratchet type, ball connector, ball chain connector, grip coupling, and/or grooved coupling, etc. The attachment unit 250, included in the first end of the coupling unit 200, enables an attachment of the coupling unit 200 to a pre-implanted anchor unit 100. Thus, an anchor unit 100 that is previously implanted at an earlier stage and permanently anchored at a cardiac valve of a patient may be used at a later stage by attaching a coupling unit 200 with the attachment unit 250 included in the first end of the coupling unit 200.

The anchor unit 100, may, when implanted, be connected to a further unit. The further unit is for instance a cardiac valve replacement unit 600 or a cardiac valve repair unit 600. The anchor unit 100 is then connected thereto via the at least one coupling unit 200.

The cardiac valve replacement unit 600 or the cardiac valve repair unit 600 can for instance be a cardiac valve prosthesis and/or an artificial cardiac valve, either a biological artificial valve or a mechanical artificial valve as illustrated in FIG. 7a) and FIG. 7b).

The purpose of a cardiac valve replacement unit 600 or a cardiac valve repair unit 600 is for instance to stop an unwanted leakage in the cardiac valve, e.g. by adding a further artificial leaflet(s) to the natural leaflets of the cardiac valve.

The cardiac valve replacement unit 600 or the cardiac valve repair unit 600 is in examples hold in place inside the cardiac valve by the connection, via the at least one coupling unit 200, to the anchor unit 100. Since the anchor unit 100 is configured to be permanently anchored at the cardiac valve, the cardiac valve replacement unit 600 or the cardiac valve repair unit 600 do not need any additional anchoring or fixation to the cardiac valve or the valve annulus by itself, as existing products on the market do, which is a huge advantage since the valve or the annulus are not rigid structures.

Existing cardiac valve replacement/repair products all need additional anchoring and fixation means on the product, often in the form of hooks and/or a stent on the side between the product and the inside of the cardiac valve.

The connection to the anchor unit 100, via the at least one coupling unit 200, eliminates this need for additional anchoring and fixation, which leads to several particular advantages.

Existing cardiac valve replacement/repair products have the same size as the cardiac valve, since they need to be anchored and fixated on the inside of the cardiac valve. In one example of the invention the cardiac valve replacement unit 600 or the cardiac valve repair unit 600 have the same size as the cardiac valve, as illustrated in FIG. 7c), however this is not a requirement.

Figure 8A:
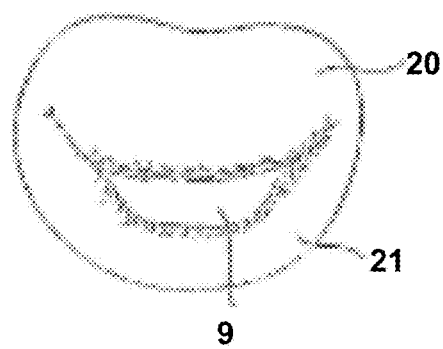
FIGS. 8a-8g are schematic illustrations of various defective cardiac valves as well as cardiac valve replacement or repair units coupled to various anchor units for treatment of the defects.
Figure 8B:
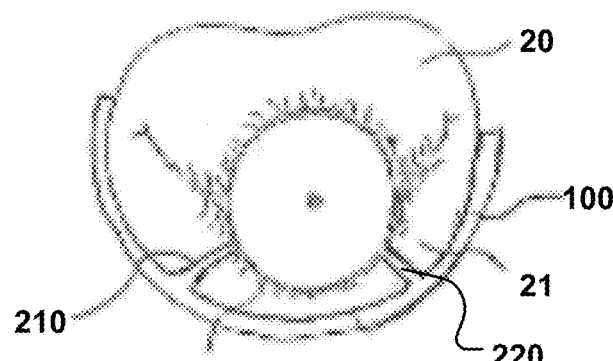

In an alternative example, the size of the cardiac valve replacement unit 600 or the cardiac valve repair unit 600 is smaller than the cardiac valve which causes a "valve in valve" effect (such as an artificial valve in a native valve), as illustrated in FIG. 8a) and FIG. 8b). The arrangement can be eccentric. In fact, the cardiac valve replacement unit 600 or the cardiac valve repair unit 600 can have any size, as long as the leakage in the cardiac valve is stopped by the cardiac valve replacement unit 600 or the cardiac valve repair unit 600.

Figure 8C:
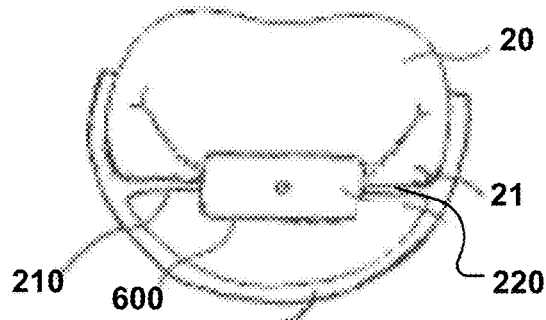

Existing cardiac valve replacement/repair products have a similar shape as the cardiac valve, often the shape of a cylinder, since they need to be anchored and fixated on the inside of the native cardiac valve. In one example of the disclosure the cardiac valve replacement unit 600 or the cardiac valve repair unit 600 have a cylindrical shape in order to resemble the shape of the cardiac valve, as illustrated in FIG. 7a), FIG. 7b), and FIG. 7c), however this is not a requirement. In another embodiment, the shape of the cardiac valve replacement unit 600 or the cardiac valve repair unit 600 is elliptical or rectangular, and smaller than the cardiac valve, as illustrated in FIG. 8a) and FIG. 8c). In fact, the cardiac valve replacement unit 600 or the cardiac valve repair unit 600 can have any shape, as long as the leakage in the cardiac valve is stopped by the cardiac valve replacement unit 600 or the cardiac valve repair unit 600.

Figure 8D:
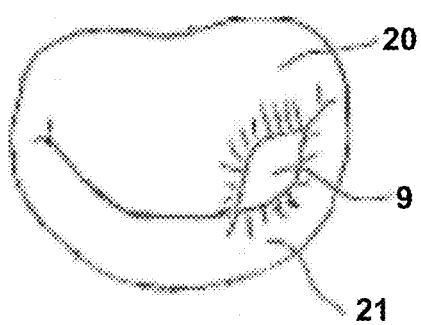
Figure 8E:
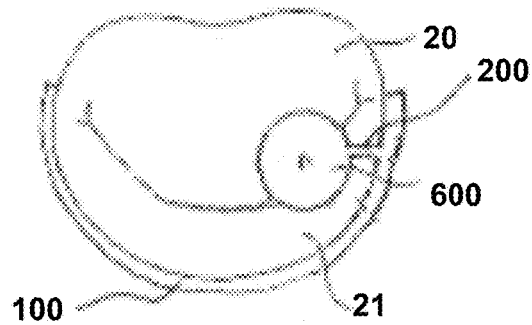
Figure 8F:
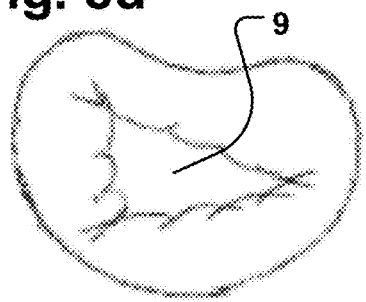
Figure 8G:
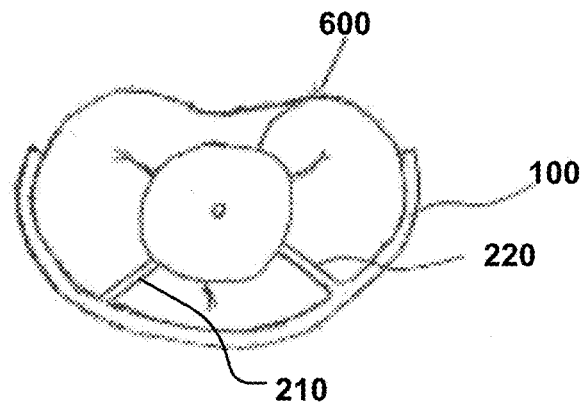

Existing cardiac valve replacement/repair products are always centered in the cardiac valve, since they need to be anchored and fixated on the inside of the cardiac valve. In one example of the disclosure the cardiac valve replacement unit 600 or the cardiac valve repair unit 600 are placed in the center of the cardiac valve, as illustrated in FIG. 7c) and also FIG. 8b) and FIG. 8c), however this is not a requirement. In another embodiment, the cardiac valve replacement unit 600 or the cardiac valve repair unit 600 is smaller than the cardiac valve and is not placed in the center of the cardiac valve, as illustrated in FIG. 8d) and FIG. 8e). In fact, the cardiac valve replacement unit 600 or the cardiac valve repair unit 600 can be placed anywhere inside the cardiac valve, as long as the leakage in the cardiac valve is stopped by the cardiac valve replacement unit 600 or the cardiac valve repair unit 600. The coupling unit 200 serves in these examples only as an attachment or fixation of the cardiac valve replacement unit 600 or the cardiac valve repair unit 600.

Existing cardiac valve replacement/repair products limit and prohibit the natural motion and movement of the cardiac valve, since they need to be anchored and fixated on the inside of the cardiac valve or cardiac valve annulus. In one example of the disclosure the cardiac valve replacement unit 600 or the cardiac valve repair unit 600 is placed inside the cardiac valve without touching or interfering with the walls of the cardiac valve and/or cardiac valve annulus, as e.g. illustrated in FIG. 8b), FIG. 8c), FIG. 8e), and FIG. 8g). In this way, the cardiac valve replacement unit 600 or the cardiac valve repair unit 600 will not limit or prohibit the natural motion and movement of the cardiac valve, and thus the cardiac valve may move freely around the cardiac valve replacement unit 600 or the cardiac valve repair unit 600.

In examples, the at least one coupling unit 200 is arranged to limit movement of a cardiac valve replacement or repair unit 600 relative the anchor unit 100.

The connection, of the cardiac valve replacement or repair unit 600 to the anchor unit 100, via the at least one coupling unit 200 enables the ability to limit and/or lock the movement of the cardiac valve replacement or repair unit 600 relative to the anchor unit 100, see FIG. 7a). This limit and/or locking of the movement of the cardiac valve replacement or repair unit 600 relative to the anchor unit 100 can be in any direction, e.g. an up and down movement, a side to side movement, and a rotational movement.

A limitation and/or locking of a longitudinal up and down movement can be of particular advantage, since the cardiac valve replacement or repair unit 600 will in this way not counter act the natural longitudinal up and down movement of the cardiac valve plane. A limitation and/or locking of a spatial side to side movement can be of particular advantage, since the cardiac valve replacement or repair unit 600 will in this way not move away from the site of leakage in the cardiac valve and will thus avoid an unnecessary leakage to occur. A limitation and/or locking of a rotational movement can be of particular advantage, since the cardiac valve replacement or repair unit 600 will in this way not cause any unnecessary damage to the leaflets of the cardiac valve.

The cardiac valve replacement or repair unit 600 is for instance arranged rotatably within a circumference of the anchor unit 100. In this manner, a threaded rotational movement of the cardiac valve replacement or repair unit 600 is provided during a cardiac cycle.

The cardiac valve can move rotationally in e.g. an annuloplasty implant during each cardiac cycle with the heart movement in a threaded up and down movement. The anchor unit 100 may be connected to both the cardiac valve replacement or repair unit 600 and the cardiac assist device 500, which may cause a larger threaded up and down movement of the anchor unit 100 along the cardiac long axis. In this way, the cardiac assist device 500 and the cardiac valve replacement or repair unit 600 cooperate in assisting the cardiac function causing an increased piston function of the cardiac valve plane.

A delivery system for a medical device as described with reference to FIG. 9, FIG. 10, FIG. 11, FIG. 12, and FIG. 13 is shown.

Figure 9:
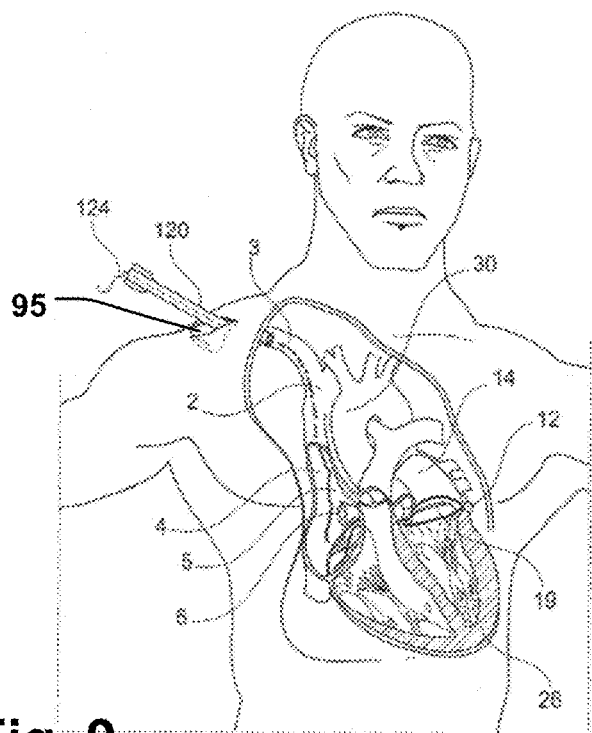
FIG. 9-11 are schematic illustrations of percutaneous transcatheter access paths to the heart.

One access to cardiac valves is through the vein system as illustrated in FIG. 9. Puncture of a large vein is done at a puncture site 95. The puncture site 95 can be the neck, thorax or in the groin. An introducer catheter 120 is put in place according to common practice.

Figure 11:
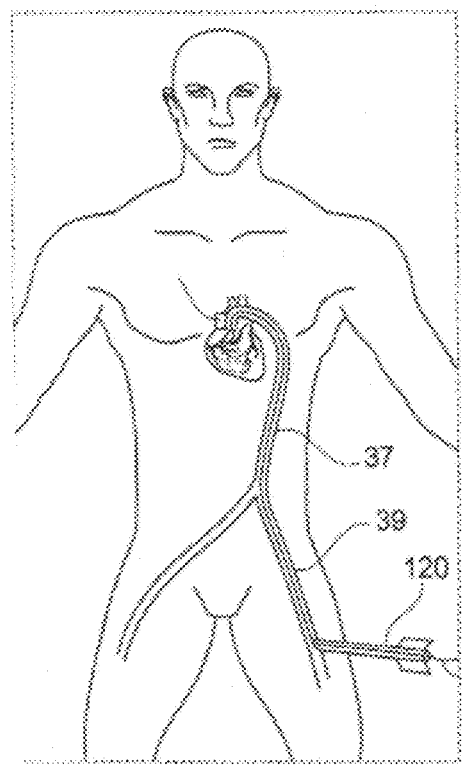

Another access to the cardiac valves is through the artery system, where an introducer catheter 120 is put in place as illustrated in FIG. 11.

Figure 12A:
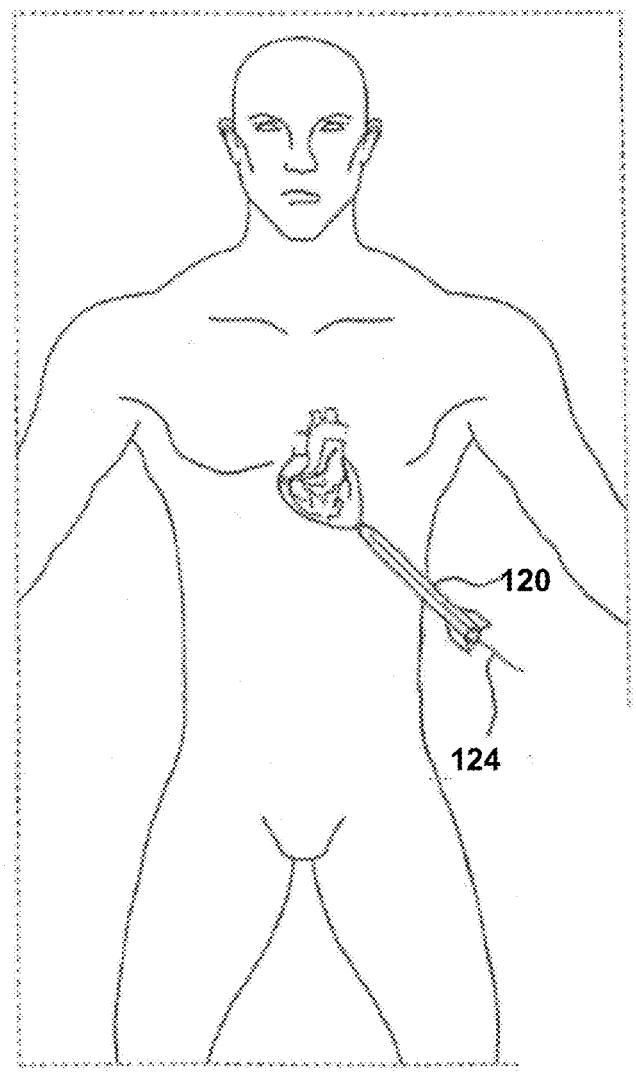
FIG. 12a-b are schematic illustrations that show a direct access path to a cardiac valve via a small incision in the chest wall.
Figure 12B:
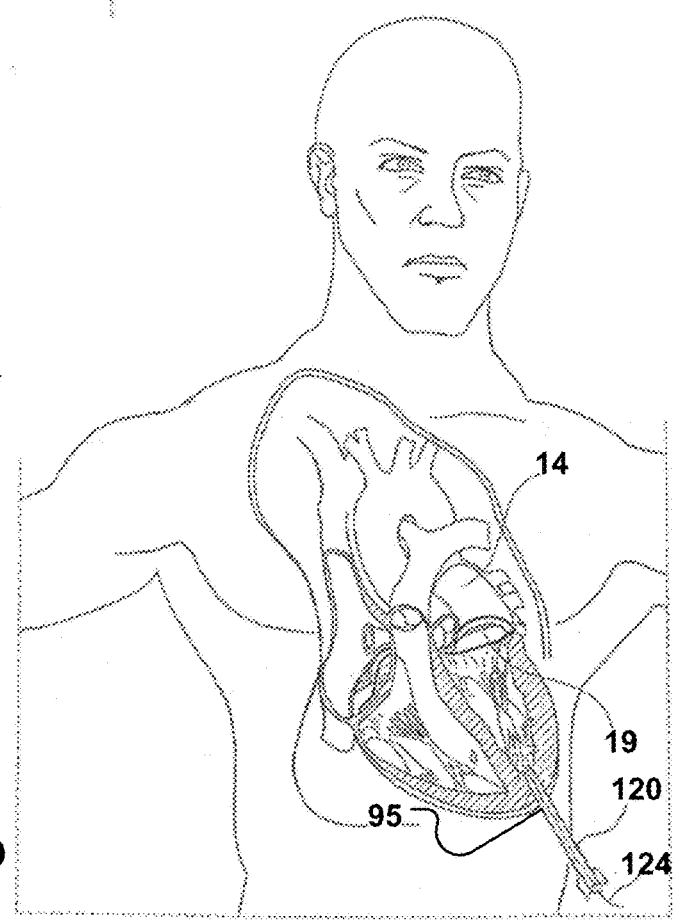
Figure 13A:
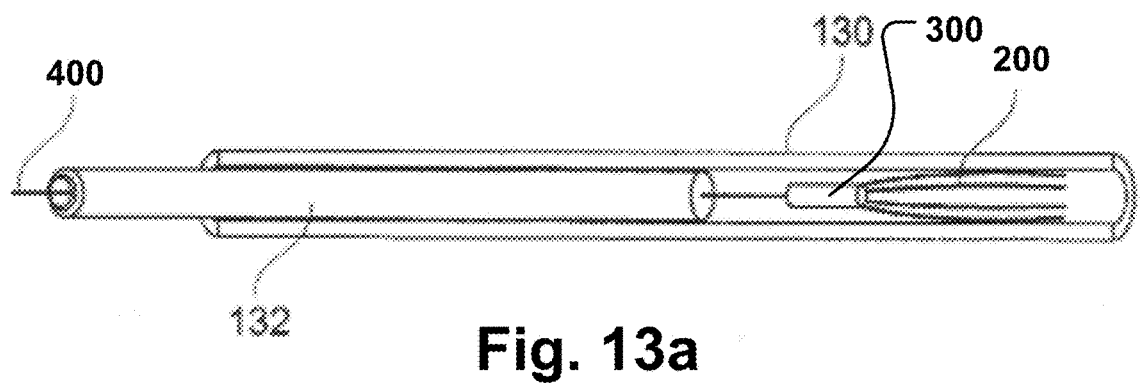
FIG. 13a-d are schematic illustrations that show a delivery system for complete catheter based insertion of coupling units based medical devices.
Figure 13B:
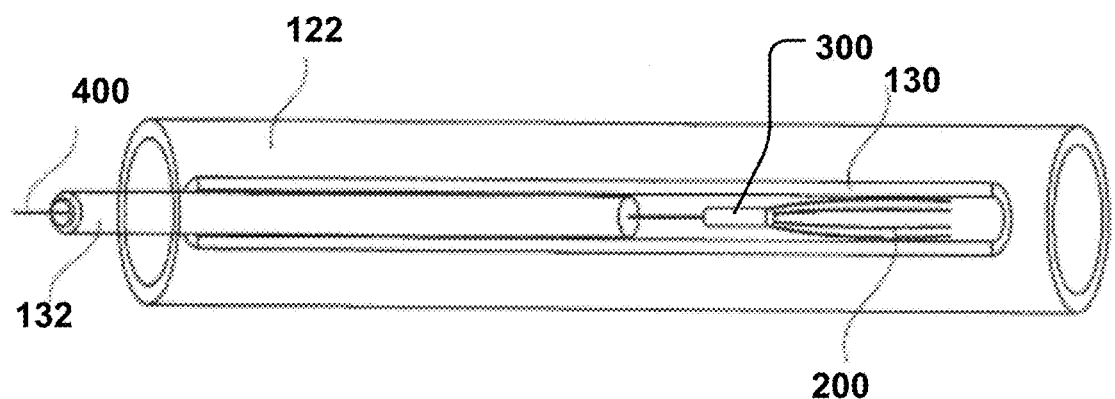
Figure 13C:
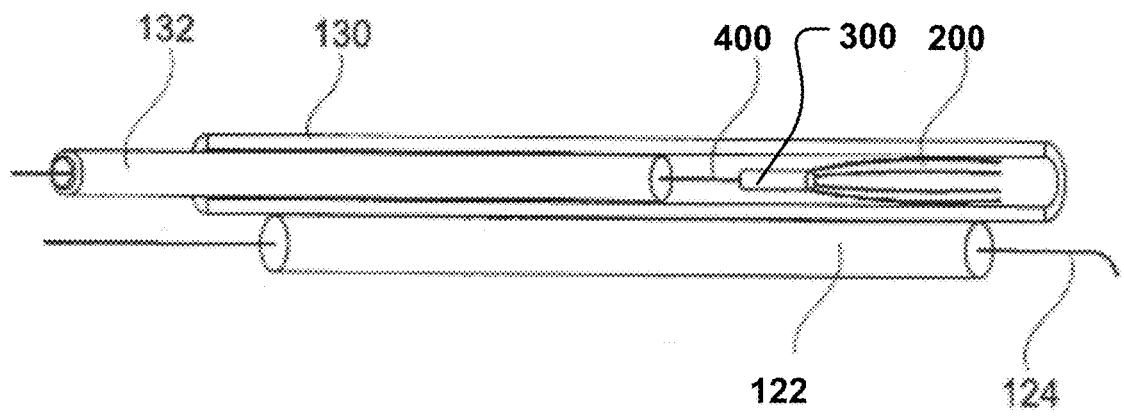
Figure 13D:
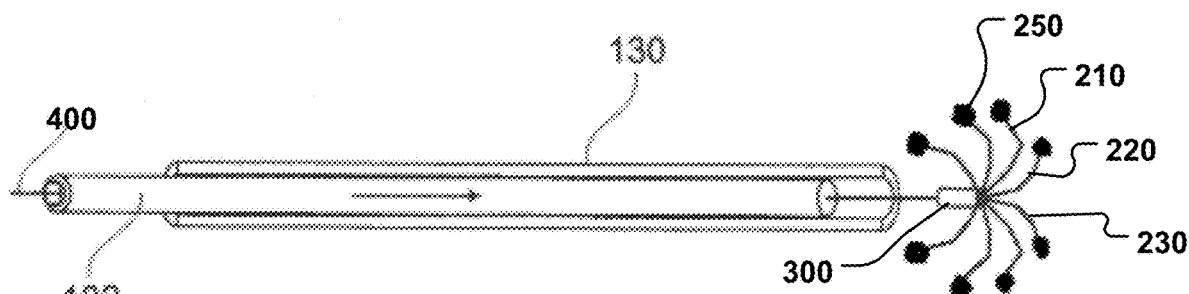

A third access to cardiac valves is through a small incision in the chest wall, giving direct access to the heart, especially the heart apex 26, again, here an introducer catheter 120 is inserted as illustrated in FIG. 12a) and FIG. 12b).

In common for different choices of access to cardiac valves is an armament of catheters, tubes, and wires that constitute delivery systems. A delivery system comprises a first delivery catheter 130 that may have an anchor unit 100 loaded inside at the tip. Such delivery catheters 130 usually have a length that reaches from the detachment site inside of a human body to outside the body, allowing direct contact with a delivery site.

A pusher tube 132 that has a smaller outer diameter than the inner diameter of the delivery catheter 130 may be advanced axially forward inside the delivery catheter 130, in order to push the anchor unit 100 out of the delivery catheter 130 at the desired site, preferably at a valve annulus.

Alternatively, the delivery catheter 130 may be retracted over the pusher tube/catheter 132, in order to deliver the device without any axial movement.

The delivery system also include guide wires 124 that may guide the delivery catheter 130 to the intended site. The guide wire 124 may run inside the delivery catheter 130, inside or next to devices, or have a separate lumen in a diagnostic/guiding catheter 122.

The anchor unit 100 may e.g. be a self-expanding stent, or a cardiac valve ring. Attachment of the anchor unit 100 to an annulus of a valve is not shown, but it may be attached with sutures 60, screws, barbs, hooks or other means of attachments.

Using similar technique, a coupling unit 200 shown in FIG. 13 is loaded inside a delivery catheter 130 in order to be inserted into heart cavities preferably the left or right atrium of a heart. Space is accommodated inside the delivery catheter 130 for the coupling unit 200 to be attached to an anchor unit 100 adjacent a cardiac valve. The pusher tube 132, accommodates a lumen for the guide wire 124 that also is permitted to run inside or next to a coupling unit 200, see FIG. 13, or alternatively have a separate lumen in a diagnostic/guiding catheter 122 as illustrated in FIG. 13. At least one coupling unit 200 is released for attachment to an anchor unit 100, permanently. Two or multiple coupling units (210, 220, 230) may be accommodated in a delivery catheter 130.

Each coupling unit 200 may comprise at least one unit.

A locking unit 300, and/or an extension unit 400 may also be included in the delivery catheter 130 as illustrated in FIG. 13

In an example of a medical procedure of implanting a medical device as described herein is disclosed. The procedure includes implementation of the elements described above. Initially an introducer catheter 120 is placed into a chosen vessel or a heart cavity. There are different scenarios:

In a first scenario a vein access is described as illustrated in FIG. 9, preferably a jugular vein on the neck, a subclavian vein on the thorax, femoral vein or more peripheral veins.

Once the introducer catheter 120 is in place, a diagnostic/guiding catheter 122 is inserted through the introducer catheter 120, and by means of a guide wire 124, placed adjacent to the delivery site adjacent to a cardiac valve.

Navigation inside the body is guided by means of x-ray such as fluoroscopy or CT scan and by means of ultrasound apparatus.

A guide wire 124 is left in place, allowing a delivery catheter 130 to travel over the guide wire 124 to the desires site. In case that the tricuspid valve, between the right atrium and the right ventricle is the target, the guide wire 124 is positioned in the right atrium.

Figure 10:
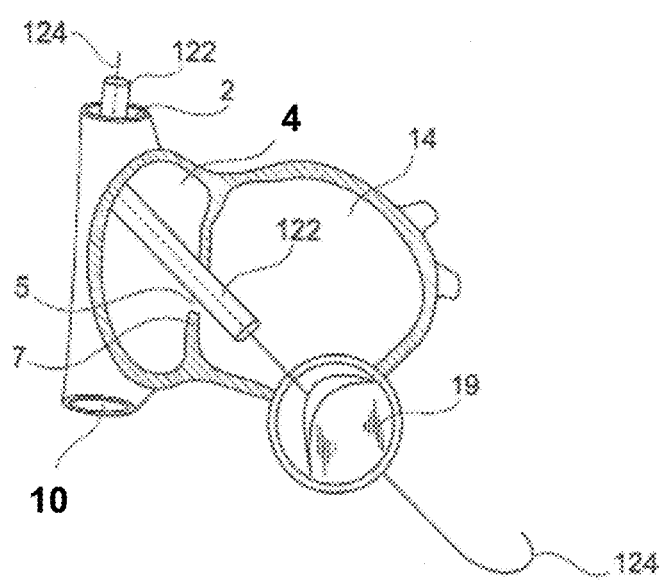

If the target is the mitral valve, a trans-septal puncture of the inter atrial septum 7 is done as illustrated in FIG. 10, and a penetration with guide wire 124 and diagnostic/guiding catheter 122 through the atrial septum between the left and the right atrium is necessary as illustrated in FIG. 10.

Once inside the left atrium, a guide wire 124 is left inside the left atrium. Over the guide wire 124 a delivery catheter 130 may advance over the guide wire 124.

If the aortic valve is the target, a guide wire 124 and delivery catheter 130 may advance through the mitral valve into the left ventricle, facing the aortic valve from below.

In a second scenario an arterial access is preferred as illustrated in FIG. 11, where a puncture of a large artery give access to the aorta by means of an introducer catheter 120. By means of guide wires 124 and diagnostic/guiding catheters 122, a guide wire 124 is placed above or below the aortic valve, allowing a delivery catheter 130 to access the desired delivery point.

If the mitral valve is the target, guide wire 124 and diagnostic/guiding catheter 122 may be advanced into the left ventricle from the aorta and even further from the left ventricle into the left atrium in order to get access to the mitral valve from above as well as from underneath.

In a third scenario an access from the heart apex is desired to get access to cardiac valves directly as illustrated in FIG. 12*a*) and FIG. 12*b*). Preferably the mitral valve and aortic valve are accessed through the left ventricle cavity, and the tricuspid valve and the pulmonary valve from the right cavity. Through a small incision in the thoracic wall and the pericardium direct access to the heart surface is obtained.

If the mitral valve is the target, an introducer catheter 120 is inserted into the left ventricle, and placed adjacent to or through the mitral valve, giving access to the mitral valve and its annulus from above or below.

A guide wire 124 may be used or considered unnecessary if the introducer catheter 120 is in the left atrium.

Once a guide wire 124 or a catheter is located next to the insertion site, the procedure is equal for all scenarios, therefore only the insertion of the here presented medical device will be described for the mitral valve from the left ventricle apex.

An anchor unit 100 may be a cardiac valve ring, previously inserted and healed in, then the new medical device will be attached to that. If the valve is native with no implant adjacent or in the valve, a procedure may be explained as follows:

With a guide wire 124 in place adjacent to the valve, the delivery catheter 130 is advanced over the guide wire 124 to the insertion site. An anchor unit 100 is advanced through the delivery catheter 130, extruded by means of the pusher tube 132 and unfolded.

Utilizing sutures 60, barbs, screws or other means not described here the anchor unit 100 is attached to the valve annulus or adjacent to it. Such anchor unit 100 may by insertion have one or more coupling units 200 attached already, preferably flexible attached to be unfolded. However, in case the coupling units 200 are not attached to the anchor unit 100, or the anchor unit 100 already is in place since previously, a coupling unit 200 will be advanced through a delivery catheter 130 to the anchor unit 100 and secured to it by means of its attachment unit 250, e.g. using the delivery system illustrated in FIG. 13.

Once the coupling unit 200 is in place, a locking unit 300 is advanced by means of delivery catheters 130 to the coupling unit 200, e.g. in order to fixate them securely. Alternatively, the locking unit 300 may be included in the delivery catheter 130 together with the coupling unit 200 as illustrated in FIG. 13. The fixation by the locking unit 300 may be between coupling units 200 (210, 220, 230 . . . ) themselves, or between coupling units 200 and anchor unit 100. By means of still another delivery catheter 130 other details may be delivered to the locking unit 300 and attached. Such details may be means for fixating tissue to the locking unit 300.

Once the assembly of the new medical device is completed inside the heart, guide wires 124 and all catheters, including introducer catheters 120 are withdrawn, and the insertion site and puncture site 95 is secured in order to prohibit bleedings.

Figure 14:
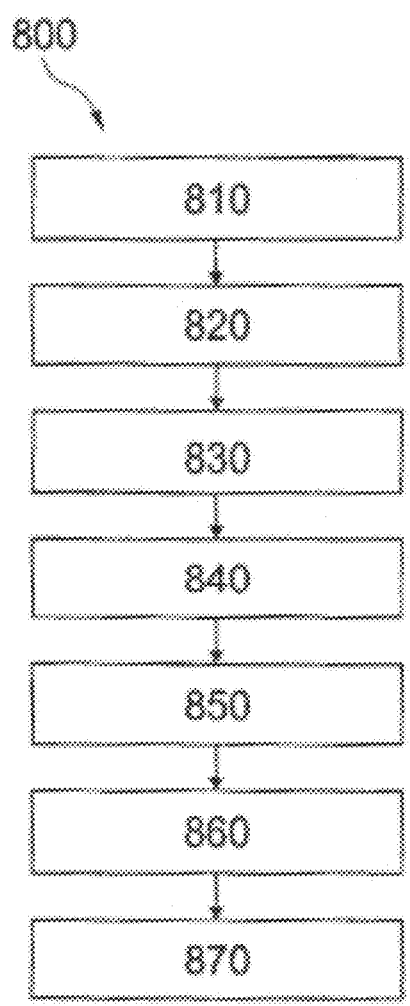
FIG. 14 is a flowchart of an example of a medical method.

In an example of a method 800 of improving function of a cardiac valve is provided as schematically illustrated in the flowchart of FIG. 14. The method is a medical procedure that involves some or all devices and systems disclosed herein.

The method 800 includes providing 810 an anchor unit 100, preferably an annuloplasty implant and more preferably a chain annuloplasty implant. Step 820 is accessing the anchor unit in the patient's body.

The anchor unit may be implanted previously or the method includes alternatively implanting 830 the anchor unit at or in the heart of the patient. Step 830 is preferably performed by transcatheter delivery. The term transcatheter means that an anchor unit like an annuloplasty ring and related devices, if any, are delivered through a catheter from outside of the patient's body to a cardiac tissue site within the patient via a catheter, i.e. a tubular elongated device to accommodate the annuloplasty ring and related devices (sequentially if so needed) in an inner lumen thereof during delivery. The catheter distal end is brought to the site while the proximal end is kept outside of the patient. The device(s) are then moved forward to the lumen until deployment out of the catheters distal end out of the catheter to the cardiac tissue site. Transcatheter delivery includes for instance intercostal access, transvascular access, transapical access, etc.

The method then includes a number of optional steps 840 to 870, whereof at least one of the steps is performed within this method 800. Several of steps 840-870 can be performed, depending on the therapy needed and combination of devices desired to achieve the therapeutic goals in the treatment of the patient.

Method 800 includes in an example stabilizing 840 the anchor unit, e.g. being a flexible annuloplasty implant. The stabilizing 840 step is performed as described above in relation to FIGS. 4a), b), c), and/or 4d).

Method 800 includes in an example fixating 850 of cardiac tissue to an anchor unit, preferably an annuloplasty implant. The fixating 850 is performed as described above in relation to FIGS. 5a) and b).

Method 800 includes in an example providing 860 cardiac assist by connecting a cardiac assist device to an anchor unit, preferably an annuloplasty implant. The connecting 860 step is performed as described above in relation to, FIG. 6. The cardiac assist device is in operation providing mechanical circulatory support for therapeutic treatment of a patient.

Method 800 includes in an example connecting 870 the anchor unit to a cardiac valve replacement or repair unit. The connecting 870 step is performed as described above in relation to FIGS. 7a), b), and c), FIG. 8a), b), c), d), e), f), and/or 8g).

The present invention has been described above with reference to specific embodiments. However, other embodiments than the above described are equally possible within the scope of the invention. The scope of the invention is only limited by the appended patent claims.

LIST OF REFERENCE SIGNS

1 Structures of the heart
2 Superior Vena Cava (SVC)
3 Subclavian Vein
4 Right atrium (RA)
5 Foramen ovale
6 Coronary Sinus (CS)
7 Inter atrial septum
8 First part of the CS
9 Leakage area
10 Inferior Vena Cava (IVC)
12 Great Cardiac Vein (GCV)
14 Left Atrium cavity (LA)
16 LA wall
18 Mitral Valve (MV) annulus
19 Whole mitral valve
20 Anterior leaflet of the mitral valve
21 The posterior leaflet of the mitral valve
22 Left Ventricular muscular wall
23 Coaptation line
24 Papillary muscles connected to the chordae
26 Apex of the left ventricle
28 Aortic valve
30 Aorta ascendens
32 Inter-ventricular muscular septum
34 Left ventricular cavity
36 Right ventricular cavity
37 Abdominal and thoracic aorta
38 Right ventricular muscular wall
39 Iliac or femoral artery
40 The tricuspid valve
48 Cardiac valve plane
49 Cardiac axis
60 Suture
95 Puncture site
100 Anchor unit
120 Introducer catheter
122 Diagnostic/guiding catheter
124 Guide wire
130 First delivery catheter
132 Pusher tube
200 Coupling unit
210 First coupling unit
220 Second coupling unit
230 Third coupling unit
250 Attachment unit
300 Locking unit
400 Extension unit
500 Driving unit (such as of a cardiac assist device)
600 Cardiac replacement or repair unit
601 $1^{st}$ Leaflet
602 $2^{nd}$ Leaflet
603 $3^{rd}$ Leaflet
610 Cage ring
800 Method
810-870 Method steps

The invention claimed is:

1. An implantable medical device including: an anchor unit configured to be permanently anchored at a cardiac valve of a patient, at least one locking unit, and a plurality of coupling units of fixed or adjustable length for connecting said anchor unit to said at least one locking unit; each coupling unit having a first end portion and a second end portion, said first end portion connectable to said anchor unit, and said second end portion including said at least one locking unit, wherein the first end portion of each of the coupling units pivotably connects the coupling unit to different positions at the anchor unit, and the second end portion of the coupling units connected to each other by the at least one the locking unit.

2. The device of claim 1, wherein said anchor unit is a flexible anchor unit and said at least one coupling unit stabilizes said anchor unit when said coupling unit is connected to said anchor unit and locked by said locking unit.

3. The device of claim 2, wherein said coupling unit includes at least one lockable arm.

4. The device of claim 2, wherein said coupling unit is locked by said locking unit to at least one other coupling unit.

5. The device of claim 2, wherein said coupling unit is locked by said locking unit to a portion of said anchor unit remote from said first end portion of said coupling unit.

6. The device of claim 1, wherein said coupling unit includes at least one arm connectable at a first end to said anchor unit and connectable remote of said first end to at least one leaflet of said valve for fixation of tissue of said cardiac valve.

7. The device of claim 1, further comprising a driving unit that is connectable to said at least one coupling unit.

8. The medical device of claim 7, wherein said locking unit includes an attachment element for releasably connecting said driving unit to said anchor unit.

9. The medical device of claim 7, wherein said coupling unit comprises at least one freely pivoting and/or rotating joint.

10. The medical device of claim 1, wherein said coupling unit includes an extension unit configured to extend from an annulus of said cardiac valve towards the apex of said heart.

11. The medical device of claim 10, wherein said extension unit has said locking unit arranged to fixate at least one leaflet and/or chordae to said extension unit to limit a range of motion thereof during the cardiac cycle.

12. The medical device of claim 10, wherein said locking unit is a device for gathering tissue of cardiac valve leaflet tissue of said cardiac valve and adapted to be attached to said extension unit and said leaflet tissue.

13. The medical device of claim 1, wherein said locking unit includes a suture having a looped portion, a clip, a clamp adapted to be crimped around one or more leaflets and/or an extension unit.

14. The medical device of claim 1, wherein said first end including an attachment unit for attaching said first end to said anchor unit.

15. The medical device of claim 1, wherein said anchor unit, when implanted, is connected to a further unit via said at least one coupling unit.

16. The medical device of claim 15, wherein said cardiac valve replacement or repair unit is arranged rotatably within a circumference of said anchor unit.

17. The medical device of claim 1, wherein said at least one coupling unit is arranged to limit movement of a cardiac valve replacement or repair unit relative said anchor unit.

18. The device of claim 1, wherein said locking unit fixes a part of a shape of said anchor unit.

19. An implantable medical device including: an anchor unit configured to be permanently anchored at a cardiac valve of a patient, at least one locking unit, and at least one coupling unit of fixed or adjustable length for connecting said anchor unit to the said at least one locking unit; the coupling unit having a first end portion and a second end portion, said first end portion connectable to said anchor unit, and said second end portion including said at least one locking unit and the coupling unit is configured to extend from an annulus of the cardiac valve towards the apex of the heart.

20. An implantable medical device including: an anchor unit configured to be permanently anchored at a cardiac valve of a patient, at least one locking unit, and at least one coupling unit of fixed or adjustable length for connecting the anchor unit to the at least one locking unit; the coupling unit having a first end portion and a second end portion, the first end portion connectable to the anchor unit, and the second end portion including the locking unit; and the anchor unit is connected to a further unit via the at least one coupling unit.

* * * * *